(12) United States Patent
Coogan et al.

(10) Patent No.: US 7,282,358 B2
(45) Date of Patent: Oct. 16, 2007

(54) MONOCHROMATIC FLUID TREATMENT SYSTEMS

(75) Inventors: John Coogan, Irving, TX (US); Barry Ressler, Weston, CT (US)

(73) Assignee: Triton Thalassic Technologies, Inc., Ridgefield, CT (US)

( * ) Notice: Subject to any disclaimer, the term of this patent is extended or adjusted under 35 U.S.C. 154(b) by 451 days.

(21) Appl. No.: 10/661,262

(22) Filed: Sep. 12, 2003

(65) Prior Publication Data

US 2004/0115612 A1    Jun. 17, 2004

Related U.S. Application Data

(63) Continuation-in-part of application No. 09/805,610, filed on Mar. 13, 2001.

(51) Int. Cl.
| | |
|---|---|
| C12N 13/00 | (2006.01) |
| A01N 1/02 | (2006.01) |
| A61L 2/00 | (2006.01) |
| A61N 1/00 | (2006.01) |
| A61N 5/00 | (2006.01) |

(52) U.S. Cl. .............. 435/173.3; 435/2; 435/173.1; 250/492.1; 422/24; 422/44

(58) Field of Classification Search .............. 436/2, 436/173.1, 173.3, 269; 422/24, 44; 250/492.1
See application file for complete search history.

(56) References Cited

U.S. PATENT DOCUMENTS

| | | | |
|---|---|---|---|
| 3,637,342 A | 1/1972 | Veloz | |
| 3,987,306 A | 10/1976 | Simpson | |
| 4,101,424 A | 7/1978 | Schooley et al. | |
| 4,608,255 A | 8/1986 | Kahn et al. | |
| 4,726,949 A | 2/1988 | Miripol et al. | |
| 4,837,484 A | 6/1989 | Eliasson et al. | |
| 4,866,282 A | 9/1989 | Miripol et al. | |
| 4,952,812 A | 8/1990 | Miripol et al. | |
| 5,030,200 A | 7/1991 | Judy et al. | |
| 5,150,705 A | 9/1992 | Stinson | |
| 5,194,740 A | 3/1993 | Kogelschatz et al. | |
| 5,232,844 A | 8/1993 | Horowitz et al. | |
| 5,290,221 A | 3/1994 | Wolf, Jr. et al. | |
| 5,433,738 A | 7/1995 | Stinson | |
| 5,446,289 A | 8/1995 | Shodeen et al. | |
| 5,597,722 A | 1/1997 | Chapman et al. | |
| 5,626,768 A * | 5/1997 | Ressler et al. ............. 210/748 |
| 5,654,443 A | 8/1997 | Wollowitz et al. | |
| 5,702,432 A | 12/1997 | Chen et al. | |
| 5,709,991 A | 1/1998 | Lin et al. | |
| 5,730,934 A | 3/1998 | Holbert | |
| 5,762,867 A | 6/1998 | D'Silva | |
| 5,789,150 A | 8/1998 | Margolis-Nunno et al. | |
| 5,798,238 A | 8/1998 | Goodrich, Jr. et al. | |
| 5,834,784 A | 11/1998 | Morgan et al. | |
| 5,843,143 A * | 12/1998 | Whitehurst ............. 607/88 |
| 5,843,374 A | 12/1998 | Sizer et al. | |
| 5,922,278 A | 7/1999 | Chapman et al. | |
| 5,951,509 A | 9/1999 | Morris | |
| 5,955,840 A | 9/1999 | Arnold et al. | |
| 6,113,566 A | 9/2000 | Schlecher | |
| 6,171,549 B1 | 1/2001 | Kent | |
| 6,171,777 B1 | 1/2001 | Cook et al. | |
| 6,190,608 B1 | 2/2001 | Laub et al. | |
| 6,190,609 B1 | 2/2001 | Chapman et al. | |
| 6,194,821 B1 | 2/2001 | Nakamura | |
| 2002/0015662 A1 * | 2/2002 | Hlavinka ............. 422/24 |

OTHER PUBLICATIONS

Oppenlander, T. "Photochemical treatment of water: Comparison of incoherent excimer lamps with a medium-pressure mercury lamp" Chem. Eng. Technol. (1998) 21(6): 502-505.*
Prodouz et al. "Use of laser-UV for inactivation of virus in blood products" Blood (1987) 70(2): 589-592.*
Kogelschatz et al. "High-intensity sources of incoherent UV and VUV excimer radiation for low-temperature materials processing" Appl. Surface Sci. (2000) 168: 29-36.*
de With et al. "UV-B-laser induced DNA damage in lymphocytes observed by single-cell gel electrophoresis" J. Photochem. Photobiol. (1994) 24: 47-53.*

(Continued)

*Primary Examiner*—Leon B Lankford, Jr.
*Assistant Examiner*—Susan Hanley
(74) *Attorney, Agent, or Firm*—McCarter & English, LLP

(57) ABSTRACT

Methods, systems and apparatus for photo-processing of fluids, particularly complex fluids, such as blood products, pharmaceuticals, injectables and vaccines, are provided. The disclosed methods and systems employ non-laser light source(s) to generate monochromatic light energy, preferably in the range of 260 nm to 310 nm, for fluid treatment. Advantageous processing regimens and/or adjunct additives and/or agents may also be used to achieve desired and/or enhanced results, e.g., inactivation of pathogens, bacteria and/or viruses, modulation of immune response, and/or leukoreduction. Particularly preferred embodiments include specific wavelengths, novel temperature control systems and geometric/structural arrangements that provide enhanced processing results and/or efficiencies. The disclosed methods, systems and apparatus achieve desirable results in a broad range of diagnostic, therapeutic and treatment applications, and generally provide enhanced operating efficiencies and/or processing results in application modalities that employ a broad range of photo-activated and/or photo-responsive materials and/or compounds.

13 Claims, 11 Drawing Sheets

OTHER PUBLICATIONS

Coogan, J. "Pathogen control in complex fluids with water-coupld excimer lamps at 282 and 308 nm" Photochemistry and Photobiology (2005) 81: 1511-1517.*

Database CAPLUS on STN, AN 1999:711834. Lomaev et al. 'Sealed Efficient Excilamps Excited by a Capacitive Discharge'. Technical Physics Letters. 1999, vol. 25, No. 11, pp. 858-859. See entire document.

Database CAPLUS on STN, AN 2000:608262. Sosnin et al. 'Capacitive Discharge Excilamps'. Proceedings of SPIE-The International Society for Optical Engineering. 2000, 3933 (Laser Applications in Microelectronic and Optoelectronic Manufacturing V), pp. 425-431. See entire document.

Database CAPLUS on STN, AN 1998:473216. Zhang et al. 'Efficient XEI Excimer Ultraviolet Sources from a Dielectric Barrier Discharge'. Journal of Applied Physics. 1998, vol. 84, No. 3, pp. 1174-1178. See entire document.

Database CAPLUS on STN, AN 1997:663032. Falkenstein et al. 'The Development of a Silent Discharge-Driven XeBr Excimer UV Light Source'. Journal of Physics D: Applied Physics. 1997, vol. 30, No. 19, pp. 2704-2710. See entire document.

PCT International Search Report, Jul. 12, 2002.

J. C. G. Doery, et al., Introduction of Aggregation of Human Blood Platelets by Ultraviolet Light: Action Spectrum and Structural Changes, Oct. 1973, vol. 42, No. 4, pp. 551-555.

D. H. Pamphilon, et al., Applications of Ultraviolet Light in the Preparation of Platelet Concentrates, 1989, vol. 29, No. 5, pp. 379-383.

G. Andreu, et al., Ultraviolet Irradiation of Platelet Concentrates: Feasibility in Transfusion Practice, vol. 30, No. 5, 1990, pp. 401-406.

Gerard Olack, et al., Improved High-Performance Liquid Chromatographic Analysis of 8-Methoxypsoralen Monoadducts and Cross-Links in Polynucleotide, DNA, and Cellular Systems: Analysis and Split-Dose Protocols, 1993, vol. 57, No. 6, pp. 941-949.

Gasparro, et al., Research Note—The Excitation of 8-Methoxypsoralen With Visible Light: Reversed Phase HPLC Quantitation of Monoadducts and Cross-Links, 1993, vol. 57, No. 6, pp. 1007-1010.

Schmitt, et al., New Trends in Photobiology (Invited Review)—Psoralen -Protein Photochemistry—a Forgotten Field, 1995, pp. 101-107.

Blundell, et al., A Prospective, Randomized Study of the Use of Platelet Concentrates Irradiated With Ultraviolet-B Light in Patients With Hematologic Malignancy, 1996, vol. 36, No. 4, pp. 296-302.

Chin, et al., Symposium-in-Print—Virucidal Treatment of Blood Protein Products with UVC Radiation, 1997, vol. 65, No. 3, pp. 432-435.

Preuss, et al., Comparison of Two Different Methods for Inactivation of Virusese in Serum, Sep. 1977, Clinical and Diagnostic Laboratory Immunology, vol. 4, No. 5, pp. 504-508.

The New England Jornal of Medicine, Leukocyte Reduction and Ultraviolet B Irradiation of Platelets to Prevent Alloimmunization and Refractoriness to Platelet Transfusions, Dec. 25, 1997, vol. 337, No. 26, pp. 1861-1869.

Corash, Inactivation of Viruses, Bacteria, Protozoa, and Leukocytes in Platelet Concentrates: Current Research Perspectives, Copyright © 1999, Transfusion Medicine Reviews, vol. 13, No. 1, pp. 18-30.

MacDonald, et al., Infrequent Detection of TT Virus Infection in Intravenous Drug Users, Prostitutes, and Homosexual Men, Mar. 1999, The Journal of Infectious Diseases, pp. 686-689.

M.L.U. del Rosario, et al., Prevention of Graft-Versus-Host Disease by Induction of Immune Tolerance With Ultraviolet B-Irradiated Leukocytes in H-2 Disparate Bone Marrow Donor, May 15, 1999, Blood, vol. 93, No. 10, pp. 3558-3564.

Goodrich, The Use of Riboflavin for the Inactivation of Pathogens in Blood Products, 2000, Vox Sanguinis, vol. 78, Supp. 2, pp. 211-215.

Prince, et al., Strategies for Evaluation of Enveloped Virus Inactivation in Red Cell Concentrates Using Hypericin, 2000, Photochemistry and Photobiology, vol. 72, No. 2, pp. 188-195.

Azuma, et al. Comparison of Sensitivity to Ultraviolet B Irradiation Between Human Lymphocytes and Hematopoietic Stem Cells, Oct. 1, 2000, Blood, vol. 96, No. 7, pp. 2632-2634.

* cited by examiner

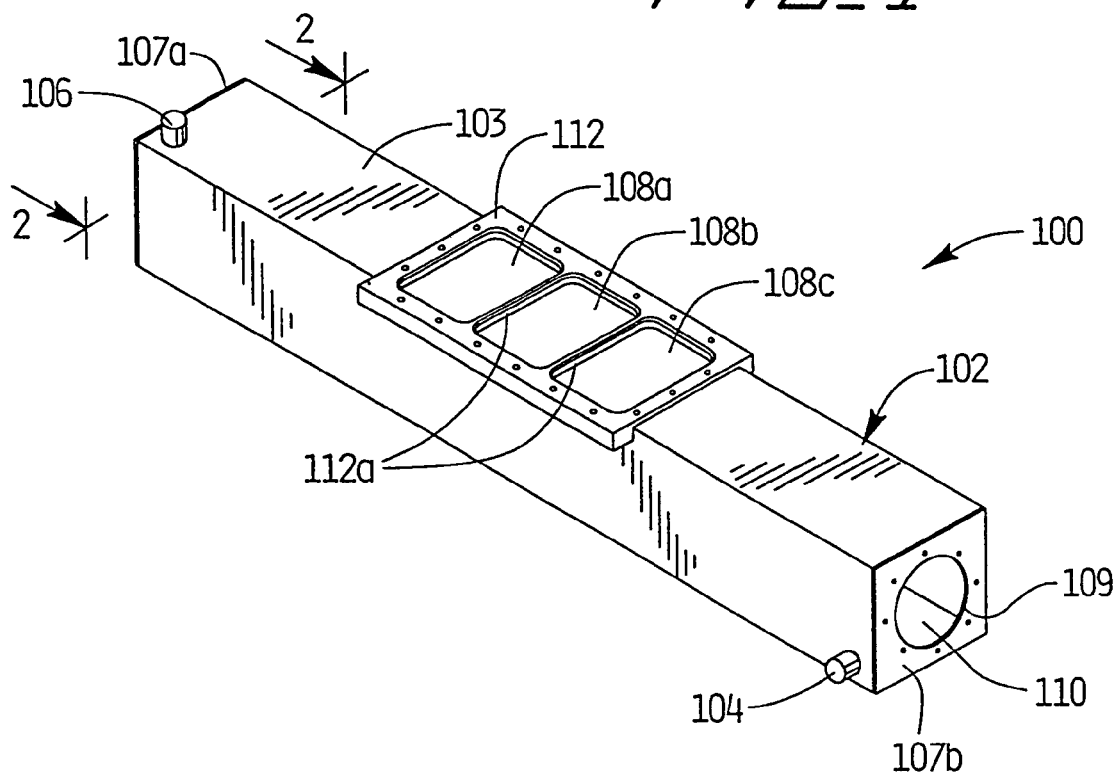
FIG_1
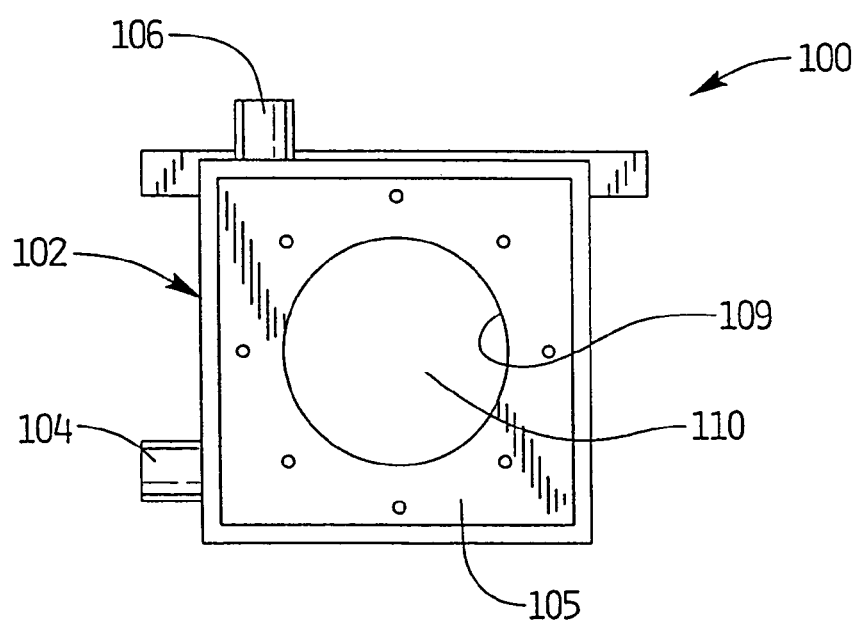
FIG_2

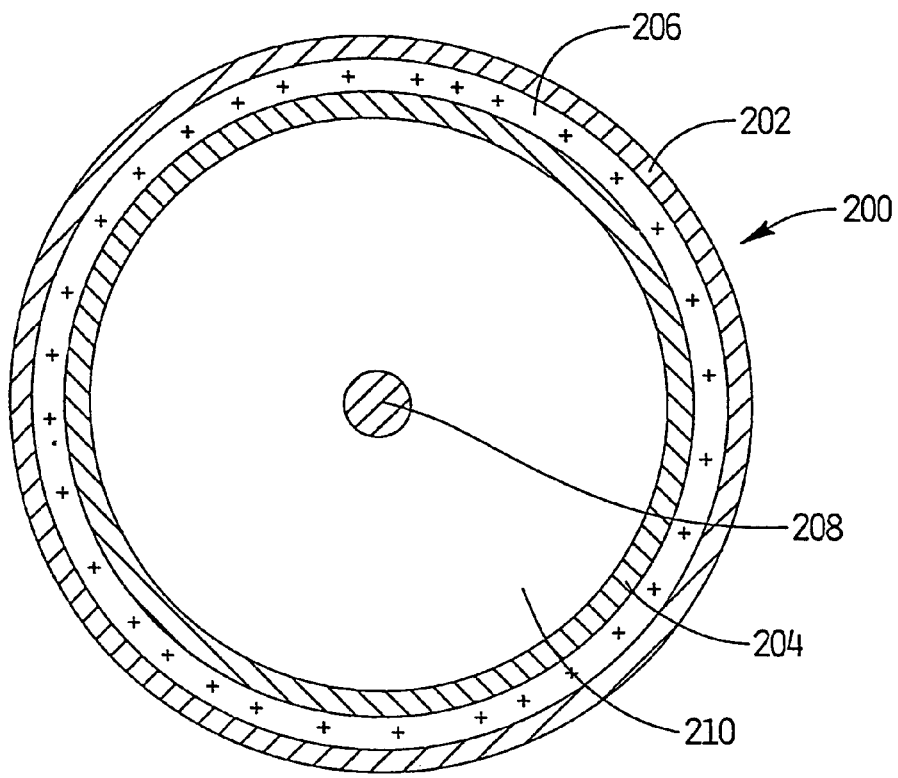
FIG_3
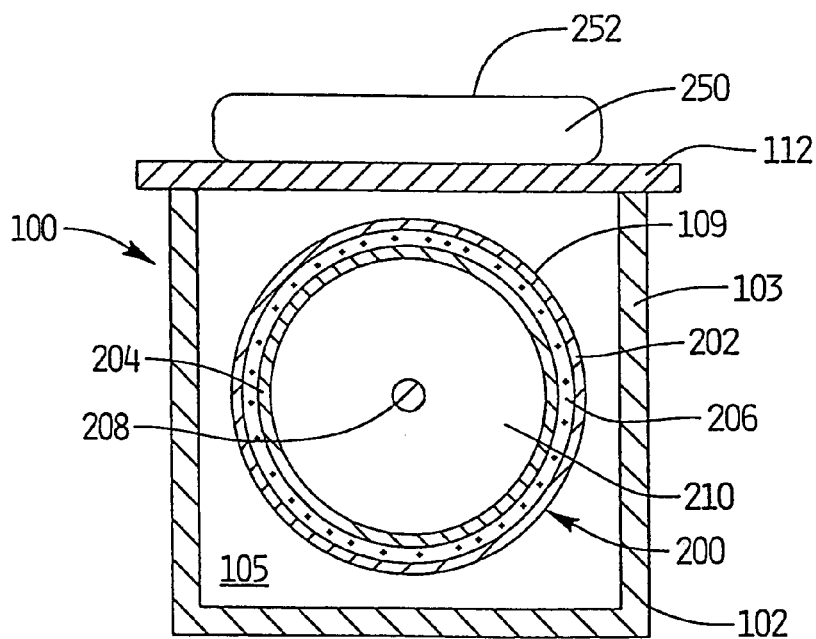
FIG_4

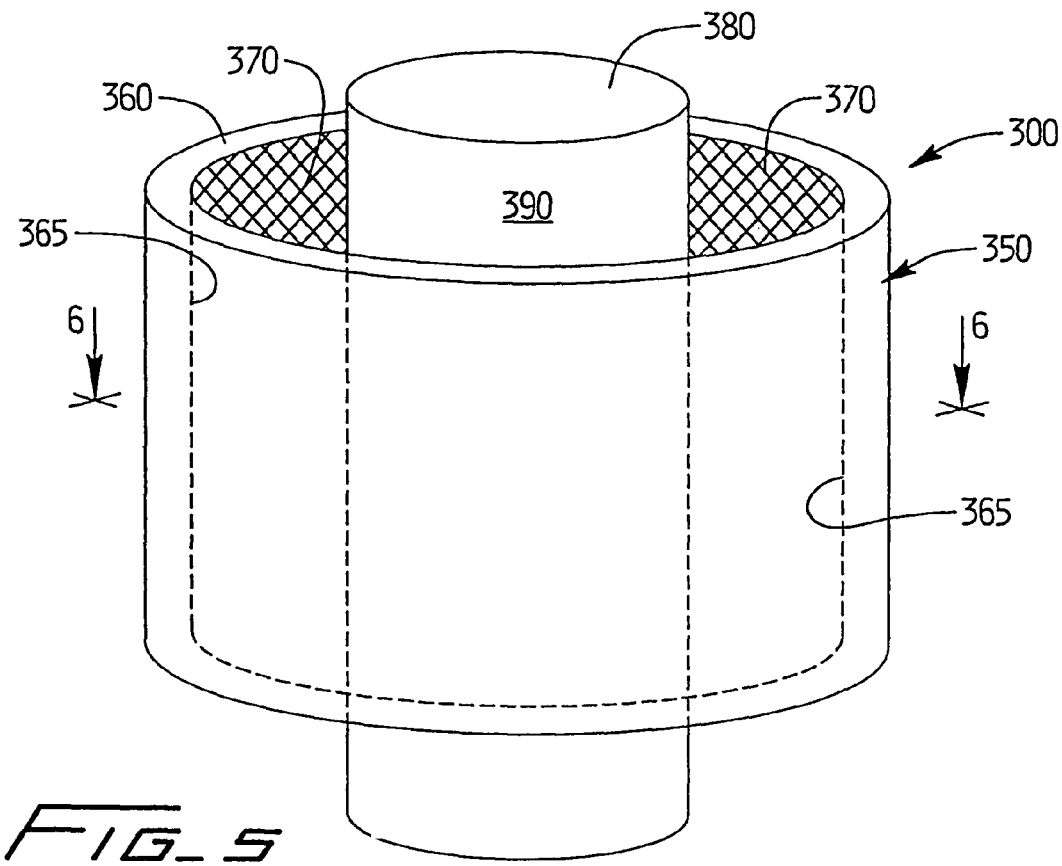
FIG_5
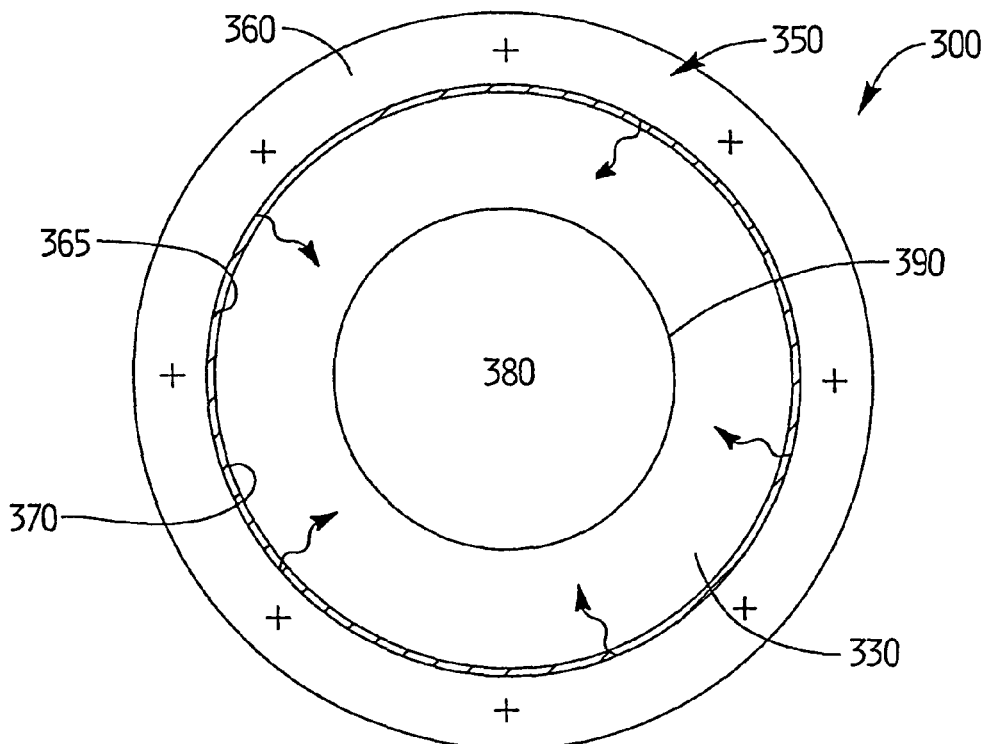
FIG_6

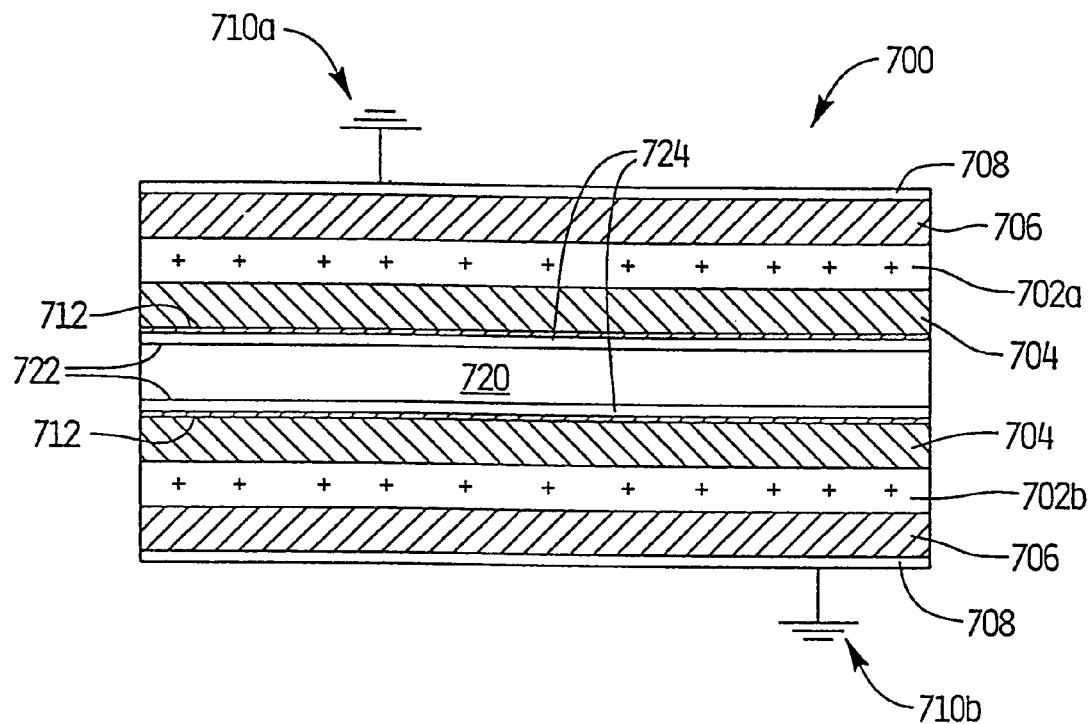
FIG_7
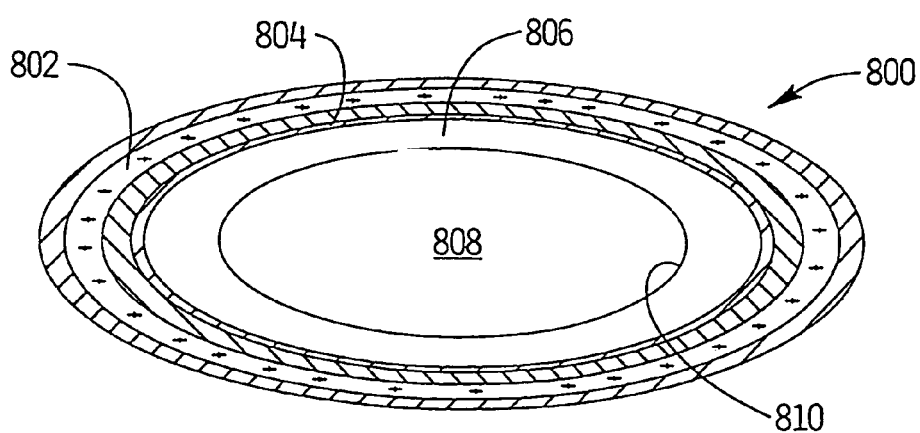
FIG_8

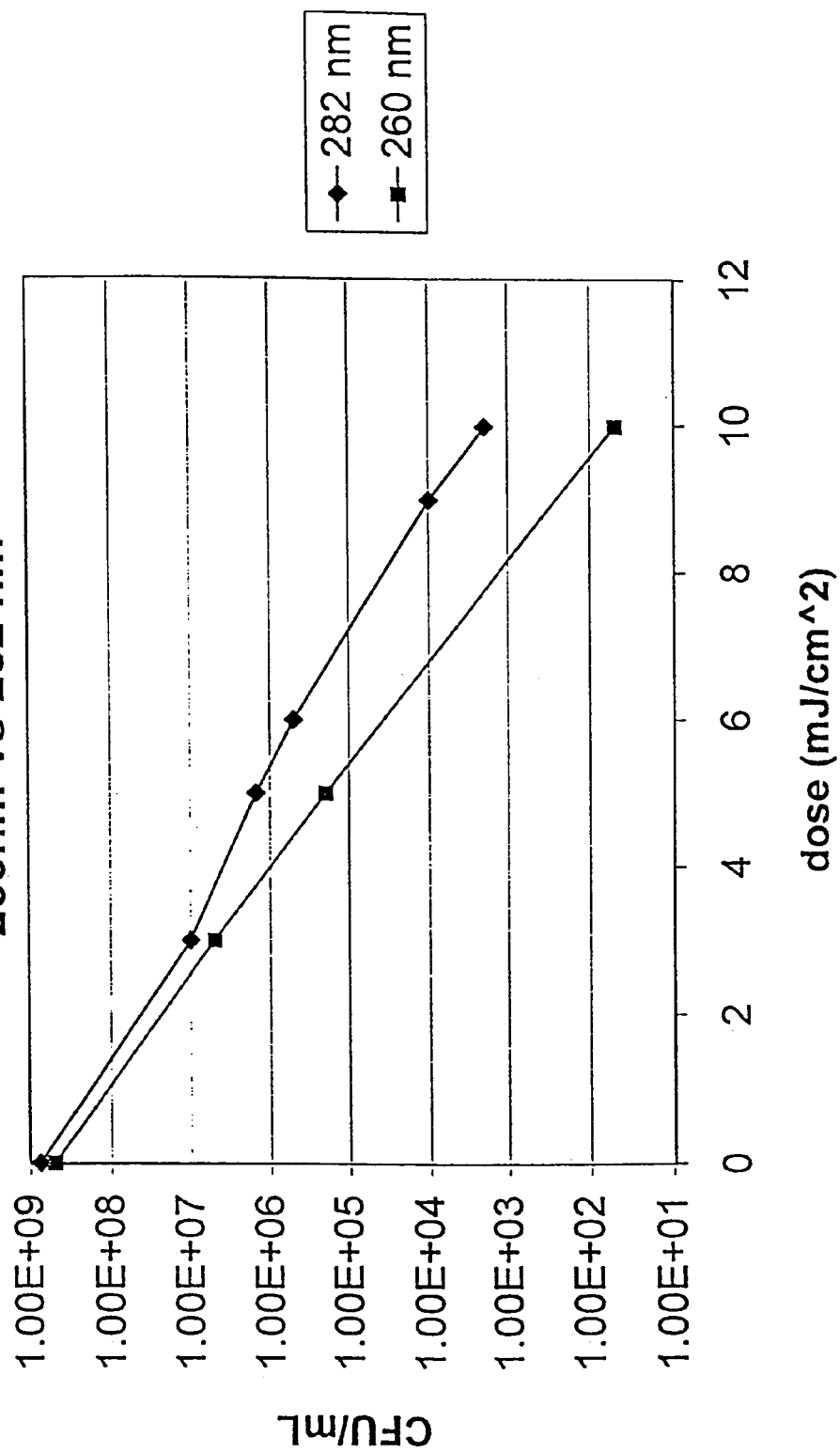

DEFINE CELL SIZE

FIG. 10a

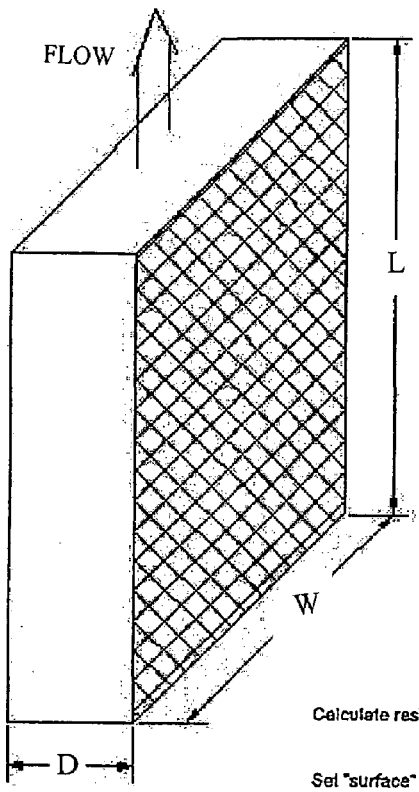

SET FLOW RATE

Depth = 1 mm

Length = 15 cm

Width = 3 cm

Cross Area = 2 Length Width     Cross Area = 90 cm$^2$

Vol. = Length Width Depth     Vol. = 4.5 cm$^3$ $$TARGET := 50 \cdot \frac{cm^3}{1 \cdot min} \qquad Duration := \frac{65 \cdot cm^3}{TARGET}$$

Duration = 78 s    Duration is time required to treat a unit of platelets

Calculate residence time    $TIME := \frac{Vol.}{TARGET}$    TIME = 5.4 s

Set "surface" dose    $SDose := \frac{depth}{(2mm)} \cdot \frac{J}{cm^2}$    Linear fit for small gaps $SDose = 0.5 \frac{J}{cm^2}$    The "Surface Dose" is based on measurements of parvo reduction as a function of platelet (and plasma) thickness.

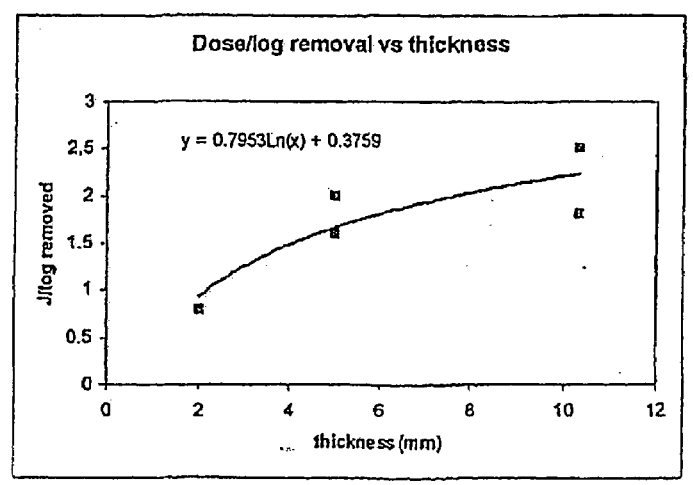

Set lamp intensity $$\text{POWERden} := \frac{\text{SDose}}{\text{TIME} \cdot 2} \qquad \text{POWERden} = 0.046 \frac{W}{cm^2}$$

Compare this intensity with other lamps $$\text{Hemalight} := 0.020 \cdot \frac{W}{cm^2} \qquad \frac{\text{POWERden}}{\text{Hemalight}} = 2.315$$

$$\text{Fluor.} := 0.008 \cdot \frac{W}{cm^2} \qquad \frac{\text{POWERden}}{\text{Fluor}} = 5.787$$

Calculate electrical parameters

Assume 15% efficeincy $$\text{ElectricalDensity} := \frac{\text{POWERden}}{0.15} \qquad \text{ElectricalDensity} = 0.309 \frac{W}{cm^2}$$

Calculate lamp power $$\text{TotPOWER} := \text{POWERden} \cdot \text{CrossArea} \cdot 2$$

$$\text{TotELEC} := \text{ElectricalDensity} \cdot \text{CrossArea} \cdot 2$$

TotPOWER = 8.333 W

TotELEC = 55.556 W

FIG. 10b

MONOCHROMATIC FLUID TREATMENT SYSTEMS

CROSS-REFERENCE TO RELATED APPLICATIONS

The present application is a continuation-in-part of a co-pending, commonly assigned U.S. patent application entitled "Monochromatic Fluid Treatment Systems," which was assigned Ser. No. 09/805,610 and was filed on Mar. 13, 2001, the entire contents of which are incorporated herein by reference.

BACKGROUND

1. Technical Field

The present disclosure relates to systems for photo-processing of fluids, and more particularly to systems for photo-processing of complex fluids, such as blood products, pharmaceuticals, injectable solutions, and vaccines using non-laser light source(s) to generate and deliver monochromatic light at advantageous wavelength(s) in advantageous systems to affect desirable results.

2. Background of Related Art

Efforts have been devoted to treatment regimens for complex fluids, e.g., fluids having medical and/or health-related uses and applications, such as vaccines, pharmaceuticals, injectable solutions, blood products and the like. These efforts have focused in part on technologies and treatment systems to remove, inhibit and/or destroy unwanted fluid components. Treatment regimens aimed at alternative objectives, such as leukoreduction (i.e., the removal of white blood cells to avoid potentially undesirable effects), have also received attention.

Significant research and development attention has focused on fluids and materials that are collected for transfusion and/or transplantation, e.g., blood products and blood components. ("Pathogen Inactivation in Labile Blood Products" in *Transfusion Medicine*, Vol. 11, pp 149-175, 2001) In assuring the safety of such materials, significant reliance is placed on pre-transfusion donor evaluation and testing. Despite current efforts, transfusions and transplantations are nonetheless implicated in the transmission of viral, bacterial and protozoan diseases. New infectious agents continue to be identified in the donor population, giving rise to increased challenges and concerns among those responsible for ensuring a safe and reliable supply of needed transfusion/transplantation materials. Testing for unknown pathogens (e.g., HIV in the late 1970's) remains problematic. Moreover, limitations necessarily exist with respect to the effectiveness of donor screening efforts, e.g., donation volumes, screening/testing impediments, logistical issues, etc. Reliable screening and/or decontamination regimens are of even greater importance for individuals receiving multiple cycles of chemotherapy and/or hematopoietic transplantation because of the cumulative risk associated with repeated transfusion/transplantation episodes.

Current research activities and perspectives in the treatment of platelets are discussed in a recently published article. (L. Corash, "Inactivation of Viruses, Bacteria, Protozoa, and Leukocytes in Platelet Concentrates: Current Research Perspectives," *Transfusion Medicine Reviews*, Vol. 13, No. 1, January, 1999). As noted in the article, risk associated with transfusion-associated infections could be reduced through development and implementation of decontamination processes that are effective against a broad array of infectious pathogens, regardless of type, including infectious agents not detected through current diagnostic tests. Decontamination processes are preferably effective against cell-free, cell-associated and latent pathogen forms. The need for this breadth in decontamination capability is exemplified by human immunodeficiency virus (HIV), which is cell-free in plasma, cell-associated in leukocytes, and in latent pro-viral form integrated into genomic leukocyte nucleic acid. Moreover, decontamination processes need to be active against a broad spectrum of bacteria, including intracellular bacterial forms, to avoid possible bacterial regrowth during storage.

Several potential inactivation technologies for treatment of platelet concentrates have been investigated/described, including psoralens activated with long-wavelength ultraviolet light, merocyanine 540 activated with visible light, riboflavin and methylene blue, and phthalocyanines activated with red light. Of these treatment technologies, attention has focused on the chemistry and associated bonding properties of different compounds, with psoralens receiving the greatest level of attention to date.

Psoralens are planar furocoumarins, many of which are synthesized by plants and ingested as foods. Psoralens preferentially bind to nucleic acid, both RNA and DNA, and vary widely with respect to solubility, nucleic acid affinity, and side reactions, e.g., active oxygen species generation. Investigations have shown that psoralen photochemical treatments can be effective for inactivation of bacteria, RNA viruses and DNA viruses. Exemplary psoralen compounds are described in U.S. Pat. No. 5,654,443 to Wollowitz et al.; U.S. Pat. No. 5,709,991 to Lin et al.; and U.S. Pat. No. 6,171,777 B1 to Cook et al.

Cerus Corporation (Concord, Calif.) has developed a series of psoralen componds that are being evaluated for their ability to inactivate pathogens in blood products. In one psoralen-based process under development by Cerus, a platelet suspension, which may be pooled from individual units from several donors, is transferred to a sterile disposable bag containing Cerus' S-59 psoralen compound. The blood-containing bag is illuminated with ultraviolet light for approximately three minutes. The Cerus procedure is intended to prevent the pathogen from reproducing and infecting a transfusion recipient. Cerus envisions the treated platelet suspension being ready for transfusion to a recipient.

The amount of psoralen required for efficient removal varies with the target species. Therefore, the inactivation levels achieved using photochemical treatment of blood products are a function of both UV dose and the concentration of the added chemical agent. The S-59 process, for example has a very strong dependence on the concentration of their proprietary psoralen, S-59. Pathogen inactivation requires 1000 times the amount of S-59 that leukocyte inactivation does. The range of UV doses required to accomplish the same task is smaller. Why? It may be that during the the experiments using S-59 it was not possible to adjust UV dose. More likely, the process is limited by the delivery of the chemical to the nucleic acid, not the activation of the chemical. From recent literature it appears that the efficacy of S-59 is limited by the kinetics of S-59 "uptake". In biological material that readily absorbs S-59 the DNA is accessible and a lower doses of additive can be used. It is believed that this same process will limit all photochemical treatments including Inactine. Recent literature (see D. C. Hooper, Emerging Infectious Diseases (7)2, 2001) has found that certain species that are resistant to psoralen-like compounds have this resistance because they are able to modify their permeability to the toxin. This theory is also supported by lab findings using S-59 that show species specific log removal rates. Some of the species that are most resistant are the same ones identified in the Hooper reference. A similar issue is the accepted inability of S-59 to inactivate preformed spores. These spores are inactivated by UV. Therefore, a combination of direct activation by UV and by photochemical may be beneficial. This is similar to issues associated with cryptosporidium and chlorine in drinking water—crypto oocysts are not inactivated by chlorine, resulting in several outbreaks of cryptosporidiosis. Cryptosporidian is inactivated by UV.

This effect is also seen in systems using riboflavin as the photosensitizer (Goodrich et al., U.S. Pat. No. 6,277,337) developed by GAMBRO BCT. However, in this work inactivation is not only a function of the target pathogen, but also on dose and wavelength of the applied light. (It is possible that the wavelength of the light source will also effect the efficacy of psoralen based processes and that this effect has not been documented due to limitations in available light sources.) The riboflavin data presented in U.S. Pat. No. 6,277,337 shows that for some organisms, specifically double-stranded viruses, a combination of visible and UV light was needed. No explanations for this requirements were made. It is possible that the inactivation of the full range of pathogens may require more than one process.

Additionally, treatment modalities based on photochemical additives require, by definition, that an external agent/material be added to the fluid being treated, with the inherent issues and uncertainties associated therewith. Moreover, beyond the requirement that external agent(s)/material(s) be added to the fluid system to effect treatment, other limitations and/or requirements have been identified with respect to certain psoralen-based treatment modalities. For example, long treatment times (up to 4 hours of UVA illumination with 8-methoxypsoralen) and reduced ambient oxygen levels associated with certain psoralen-based systems are not compatible with requirements for ease of operation, e.g., in clinical blood bank environments. In addition, the addition of a free radical quencher, e.g., rutin (a naturally occurring flavenoid), may be required to prevent platelet damage due to active oxygen species, i.e., to preserve in vitro platelet function. The addition of free radical quencher(s) like rutin further increases the complexity of treatment systems.

As discussed by Corash, high UVA doses have also been required for certain psoralen compounds, e.g., from 24 to 70 J/cm$^2$ for 4'-(amino-methyl)-4,5', 8-trimethlypsoralen (AMT), to treat platelet suspensions in 100% plasma. AMT has also exhibited questionable toxicology profiles. Reductions in plasma protein concentration, e.g., to 15% through use of synthetic platelet additive solution, is effective in reducing energy requirements, e.g., viral inactivation with AMT at 2.4 J/cm$^2$, but is not practical for large-scale operations. (*Transfusion Medicine Reviews*, Vol. 13, No. 1, pp. 21, 23.)

Margolis-Nunno et al. evaluated the treatment of HIV-infected platelet concentrates with an AMT/rutin system using two types of ultraviolet radiation, UVA and UVA1. UVA was characterized as broad-band ultraviolet A light, having a wavelength of between 320 and 400 nm, and UVA1 was characterized as narrow-band UVA light, having a wavelength between 360 and 370 nm. Margolis-Nunno et al. concluded that wavelength was an important consideration in these treatment systems and that, at similar fluences, the tested UVA was more injurious to platelets than was UVA1. (Margolis-Nummo et al., "Psoralen-Mediated Photodecontamination of Platelet Concentrates: Inactivation of Cell-free and Cell-associated Forms of Human Immunodeficiency Virus and Assessment of Platelet Function In Vivo," *Transfusion*, Vol. 37, September 1997, pp. 889-895.)

Photodynamic therapy (PDT) has also received significant research and development attention, particularly for cancer indications. In typical PDT treatment regimens, a photosensitizer is administered systemically, e.g., a porphyrin derivative, and after a period in which the photosensitizer accumulates within a target tissue, a measured amount of light is applied to the target region. Beyond cancer treatment, PDT treatments have been developed for use against ophthalmological conditions, cardiovascular conditions (e.g., artherosclerosis and restenosis), and immune-mediated conditions (e.g., psoriasis).

El-Ghorr and Norval describe the biological effects of narrow-band UVB irradiation, e.g., in treating psoriasis, as compared to conventional broadband UVB irradiation effects. (El-Ghorr et al., "Biological Effects of Narrow-Band (311 nm TL01) UVB Irradiation: A Review," Journal of Photochemistry and Photobiology B: Biology 38 (1997), 99-106.) The TL01 lamp tested by El-Ghorr and Norval emits a narrow peak (51% of the radiant energy at 311 nm). Based on limited available test data, the TL01 lamp appears to be more suppressive than broad-band UVB during phototherapy with respect to natural killer cell activity and the function of mononuclear cells, as measured by lymphoproliferation and cytokine production. El-Ghorr and Norval suggest that the noted effect of the TL01 lamp may be both dose related and wavelength dependent.

In a further study, Prodouz et al. evaluated the use of laser-UV in treating blood products to inactivate poliovirus. (Prodouz et al., "Use of Laser-UV for Inactivation of Virus in Blood Products," *Blood*, Vol. 70, No. 2, August, 1987, pp. 589-592.) The Prodouz et al. study uniformly irradiated samples with a XeCl excimer laser that delivered 40 nsec pulses of UV at 308 nm. This work noticed that at higher powers, including the very high peak power delivered from the pulsed laser, there was a greater reduction in platelet function. Even still, Prodouz et al. concluded that, when using a pulsed excimer laser at 308 nm, there exists a window of efficacy for exposure doses between 10.8 and 21.5 J/cm$^2$ and peak intensities of less than 0.17 MW/cm$^2$ within which a hardy virus is significantly inactivated and platelet and plasma proteins are minimally affected. This work inactivate polio virus. The efficacy of 308 nm on more complex targets has not been determined.

Andreu et al. evaluated ultraviolet irradiation of platelet concentrates to reduce HLA immunization by placing suspended platelet concentrates between quartz plates and irradiating with UV-B rays at 310 nm. Andreu et al. concluded that in vitro function of platelet concentrates remains unaffected by UV-B up to 2.25 J/cm$^2$, but that higher energies inhibit the aggregation induced by ADP and collagen. Andreu et al. identified a gap in treatment effects with UV-B rays between 0.2 J/cm$^2$, where the desired inhibitory effect on immunologic recognition is probably complete, and above 2 J/cm$^2$, where detrimental effect on platelet function appears. (Andreu et al., "Ultraviolet Irradiation of Platelet Concentrates: Feasibility in Transfusion Practice," *Transfusion*, Vol. 30, No. 5-1990, pp. 401-406.)

U.S. Pat. Nos. 4,726,949; 4,866,282; and 4,952,812 to Miripol et al. disclose blood product irradiation methods and systems for inactivating white blood cells. The Miripol et al. treatment regimens employ ultraviolet radiation predominantly of a wavelength of 280 to 320 nm, an intensity of 4 to 20 mW/cm$^2$, and a total energy exposure of 800 to 20,000 mJ/cm$^2$. Eight to twelve conventional, high intensity bulbs are described for use in irradiating blood contained within a flexible, collapsible poly(ethylene-vinyl) acetate plastic bag, the plastic bag typically being stretched on a framework. An exhaust fan is provided in the back of the Miripol et al. apparatus to exhaust heat generated by the high intensity bulbs. It is interesting to note that while in this work it was claimed that the process was novel because it operated at a different surface dose (J/cm2), a closer read of the data shows that the applied surface dose required for a successful treatment increases with the thickness of the blood product. The critical parameter is therefore not the applied surface dose, but how that dose is distributed within the fluid volume.

Despite efforts to date, there exists a continuing need for systems that facilitate treatment of complex fluids, e.g., blood products, pharmaceuticals, injectable solutions and vaccines. In particular, systems applicable to high value/complex fluids that effectively and reliably achieve desirable levels of pathogen inactivation, modulation of immune response, medical therapy and/or chemical synthesis, without negatively impacting desirable characteristics of the high value/complex fluid, are needed. While significant attention has been devoted to developing and evaluating a variety of photosensitive agents in treating pathogens and the like, the potential effects and/or influences of light source(s) and/or wavelength characteristics of light on complex fluid treatment systems have received less intensive study. While UV-B irradiation is considered an option for leukocyte inactivation pathogen using only UV light is not considered a viable process. Indeed, Cook et al. state that treatment of blood products to eliminate transmission of diseases by inactivating pathogens through UV alone is "completely incompatible with maintenance of red cell function." (U.S. Pat. No. 6,171,777 B1, col. 2, lines 58-64.) A more recent review of "Pathogen Inactivation of Labile Blood Products (*Transfusion Medicine*, Vol. 11, 149-175, 2001), did not consider chemical free processing of pathogens using UV light.

SUMMARY OF THE DISCLOSURE

The present disclosure provides innovative systems for photo-processing of fluids, particularly high value and/or complex fluids, such as blood products, pharmaceuticals, injectable solutions and vaccines. The disclosed systems employ advantageous light source(s) and processing regimens, whether alone or in combination with adjunct additives and/or photoactive agents, to achieve desired results. Preferred systems according to the present disclosure are effective in inactivating pathogens, bacteria and/or viruses, modulation of immune response, and/or leukoreduction, without negatively impacting desirable components and/or attributes of the treated fluid, and achieve desirable results in a broad range of diagnostic, therapeutic and treatment applications. Preferred systems further provide enhanced operating efficiencies and/or processing results in application modalities that employ a broad range of photo-activated and/or photo-responsive materials and/or compounds.

One advantageous aspect of the disclosed systems relates to an ability to utilize light energy to limit and/or minimize degradation of certain fluid properties and/or components, e.g., potential degradation through heat, energy activation or the like, while simultaneously maximizing the desired effect (s) through use of such light energy. The desired effects may be biologic, e.g., pathogen inactivation, or chemical, e.g., excitation of specific psoralen-based adducts, or a combination thereof. The generation of harmful and/or toxic byproducts is also advantageously minimized or avoided according to the present disclosure.

As described earlier there are limitations in the range of pathogens inactivated by either photosensitized reactions (particularly using psoralen or riboflavin) or light. The ability to initiate both photosensitized inactivation, and direct UV disinfection with a single source is therefore appealing. This work proposes such a system. In this process UV light in the range of 282 of 320 nm is applied, 290 and 308 nm are specifically highlighted. This light activates photosensitized reactions of larger genome pathogens best treated photochemically, as well as smaller single stranded targets best inactivated by light alone.

According to the present disclosure, light source(s) are provided that supply light energy having highly advantageous effect(s) on treated fluids, particularly high value and/or complex fluids such as blood products, pharmaceuticals, injectable solutions and vaccines. The present disclosure further provides system design and processing regimens that, when used in conjunction with disclosed light source (s), provide advantageous fluid processing results, both in batch and continuous flow treatment systems.

The present disclosure is also directed to a method for treating a complex fluid which includes introducing a supply of complex fluid into a treatment zone, the complex fluid including a nucleic acid; adding a photoactive compound to the complex fluid; and applying light energy to the complex fluid and the photoactive compound in said treatment zone. The light energy is supplied from a light source that generates light energy having a designated wavelength below 340 nm. The light energy from the light source is effective to substantially excite said nucleic acid of the complex fluid and to substantially excite said photoactive compound.

Preferably, the complex fluid is a blood-based product and further includes biological proteins which are inactivated by ultraviolet light. Additionally, it is presently envisioned that the light source is a non-laser light source and said light energy from the non-laser light source is substantially monochromatic. Alternatively, the light source is configured to produce polychromatic output. In a preferred embodiment, the light source selectively adjusts a gas mixture containing a rare gas or halogen so as to produce the polychromatic output.

It is envisioned that the photoactive compound used in the disclosed method can be riboflavin. Additionally, the nucleic acid excited by the light energy from the light source is single stranded and belongs to a pathogen and the photoactive compound is effective at inactivating pathogens with double stranded nucleic acid.

BRIEF DESCRIPTION OF FIGURE(S)

To assist those of skill in the art to which the subject matter of the present disclosure appertains, reference is made to the accompanying drawings and associated detailed description, in which:

FIG. 1 is a perspective view of one aspect of a treatment apparatus according to an embodiment of the present disclosure;

FIG. 2 is a cross sectional view of a first aspect of the treatment apparatus of FIG. 1, taken along line 2-2;

FIG. 3 is a schematic cross sectional view of a second aspect of a treatment apparatus according to an embodiment of the present disclosure;

FIG. 4 is a schematic cross sectional view of combined first and second aspects of a treatment apparatus according to an embodiment of the present disclosure;

FIG. 5 is a schematic perspective view of a treatment apparatus according to an alternative embodiment of the present disclosure;

FIG. 6 is a schematic cross sectional view of the treatment apparatus of FIG. 5, taken along line 6-6;

FIG. 7 is a schematic cross sectional view of a treatment apparatus according to a further alternative embodiment of the present disclosure;

FIG. 8 is a schematic cross sectional view of a treatment apparatus according to an additional alternative embodiment of the present disclosure;

FIG. 9 is a graphical representation which illustrates the *e-coli* dose response based on experimental results obtained according to an embodiment of the present disclosure;

Figure 11B:
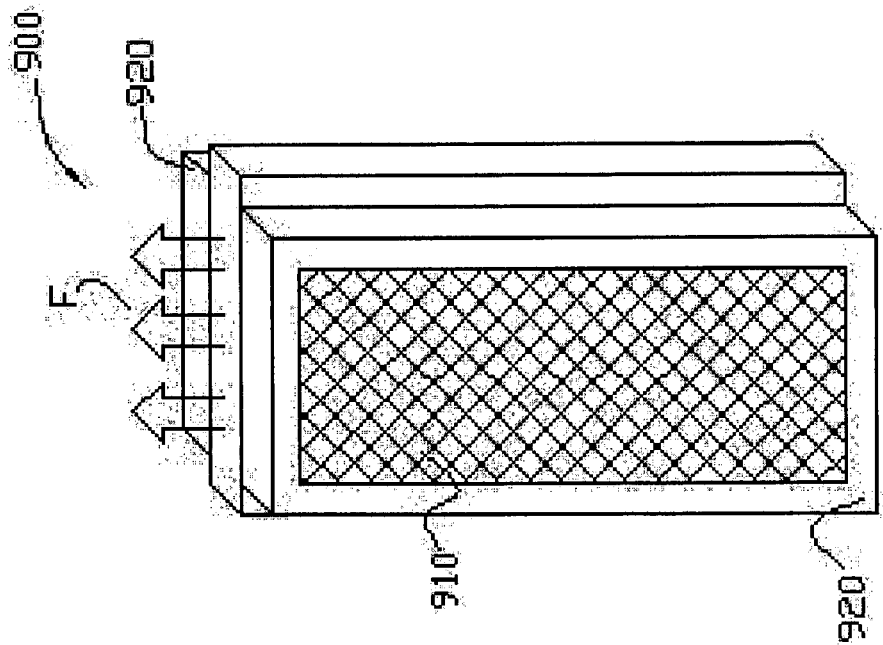
Figure 11A:
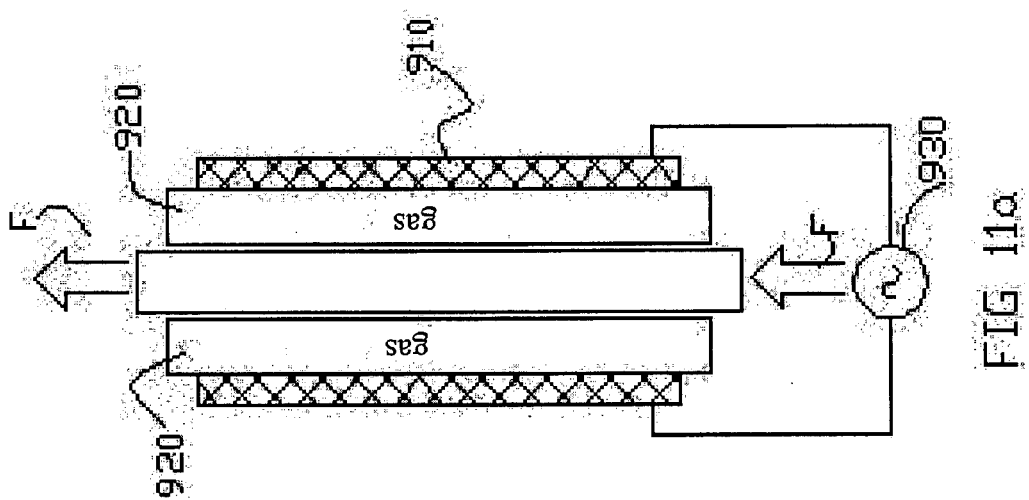
Figure 12A:
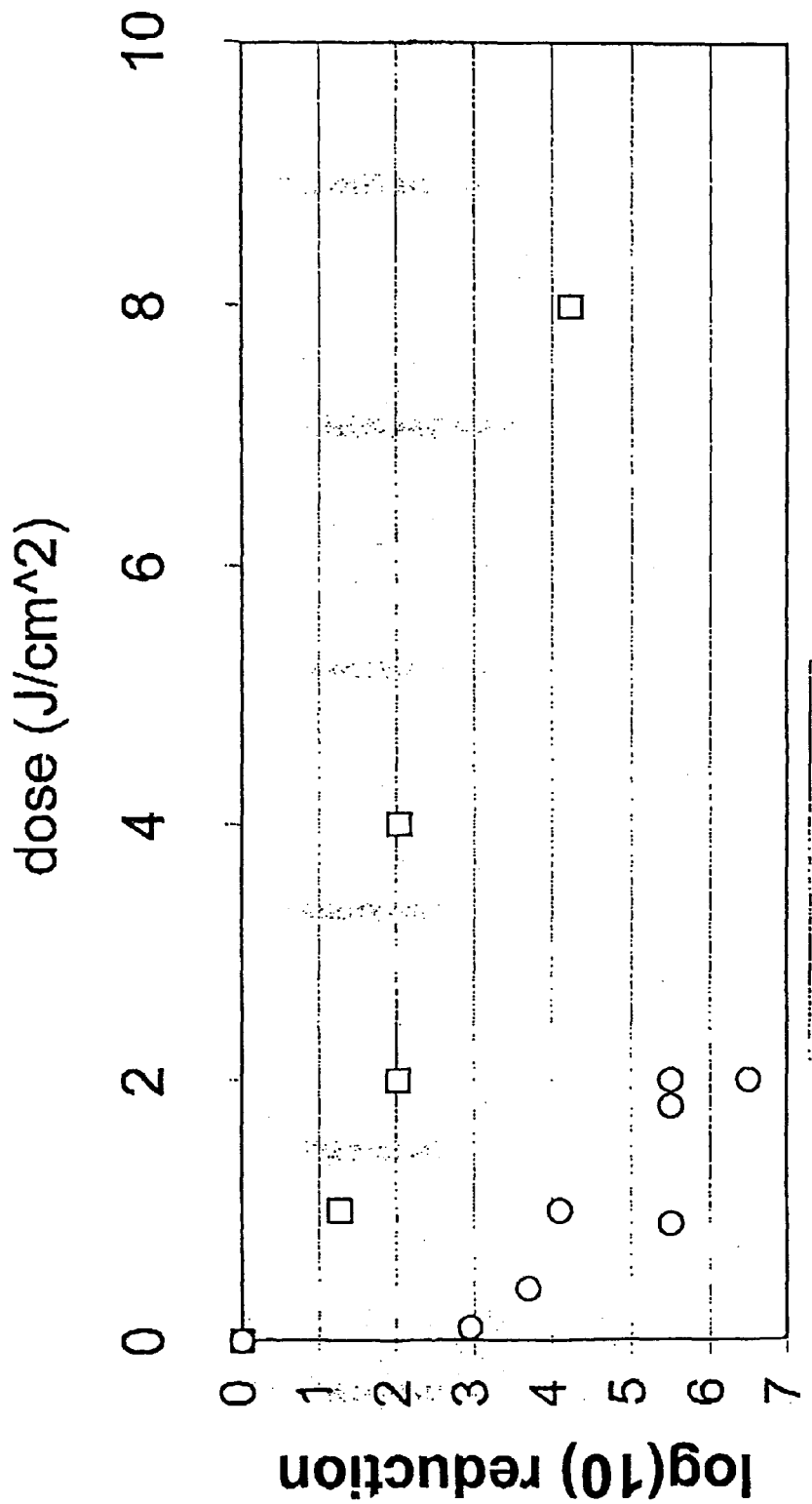
Figure 12B:
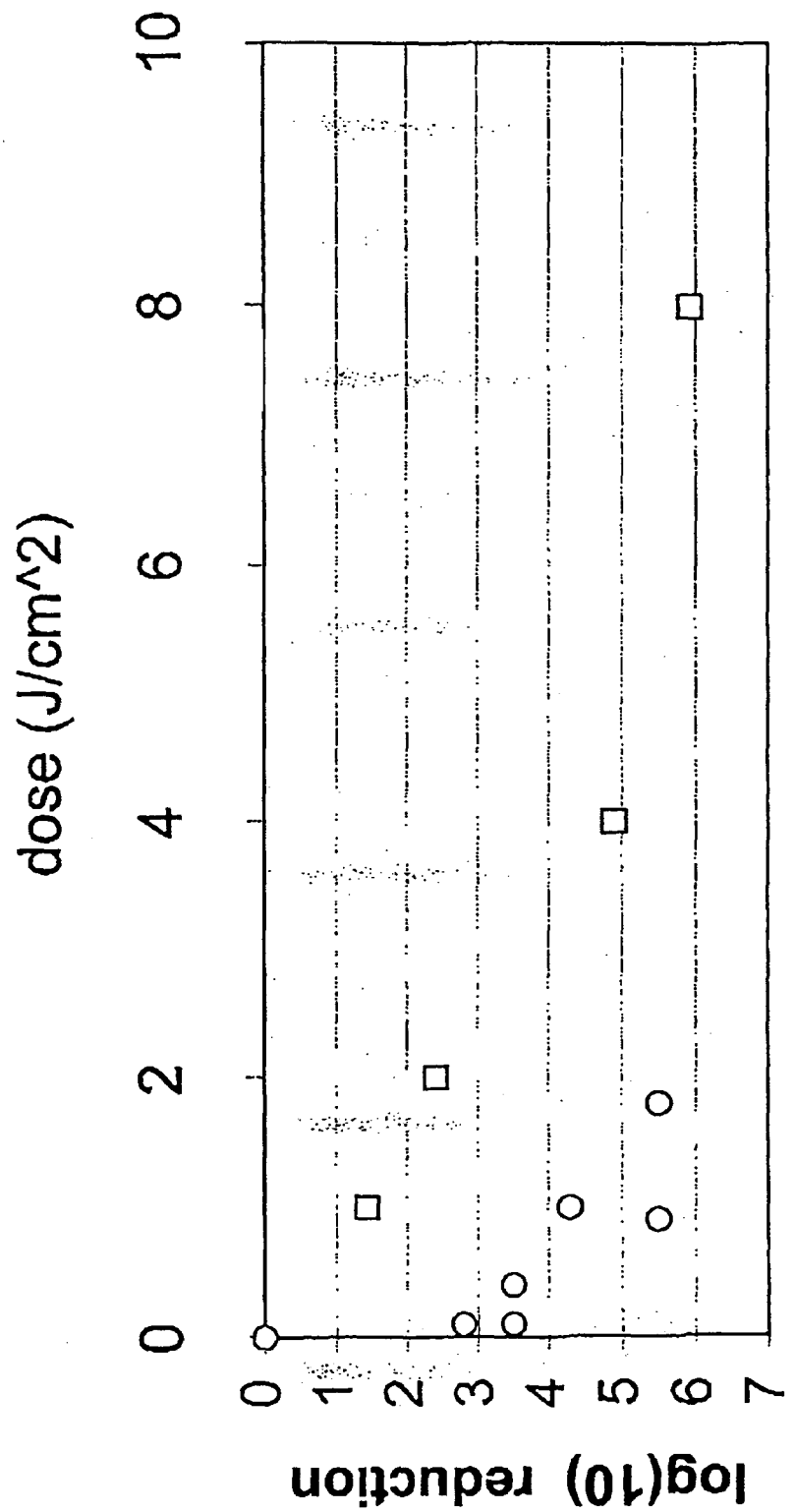
Figure 13:
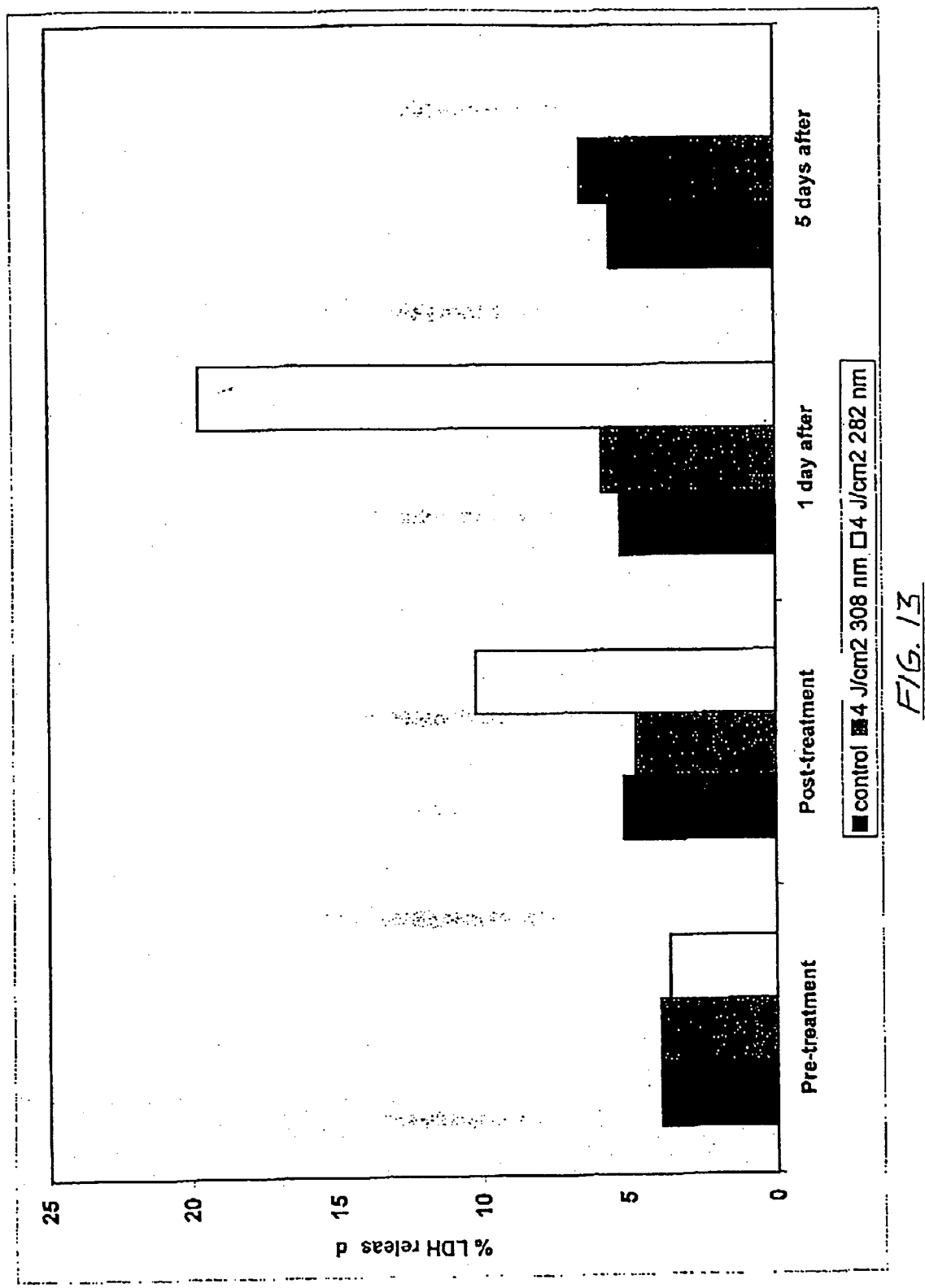

FIGS. 10a and 10b demonstrate an algorithm for maximizing the thickness of fluids within the treatment systems described here;

FIG. 11a is side elevational view of a reactor/lamp embodiment of the present disclosure which is well suited for flow through applications;

FIG. 11b is a front elevational view of the lamp of FIG. 11a;

FIGS. 12a-12b summarize the inactivation of PPV at 282 nm and 308 nm in samples of random donor platelets and fresh frozen plasma; and FIG. 13 is a graphical representation which summarizes the amount of LDH released from platelets during processing at 282 and 308 nm. LDH is used as a measure of cellular damage.

DETAILED DESCRIPTION OF PREFERRED EMBODIMENT(S)

The present disclosure provides innovative systems for photo-processing of fluids, particularly high value and/or complex fluids, such as blood products, pharmaceuticals, injectable solutions and vaccines. As used herein, a "complex fluid" is a fluid that includes a plurality of fluid components that are sensitive to and/or activated by light and/or heat energy, wherein a first light-sensitive/light-activated/heat-sensitive fluid component is to be substantially preserved according to the disclosed treatment regimen, and a second light-sensitive/light-activated fluid component is to be substantially modified, inactivated and/or eliminated according to the treatment regimen. A "complex fluid" according to the present disclosure may also include added photoactive compound(s)/material(s), e.g., psoralen, and light energy sensitivity/reactivity may be due in part to the presence of such photoactive compound(s)/material(s).

The innovative systems of the present disclosure employ advantageous light source(s) and processing regimens unique to the treatment of complex fluids. The disclosed systems may be employed with or without photoactive compounds and/or agents to achieve desired results, e.g., inactivation of pathogens, bacteria and/or viruses, modulation of immune response and/or leukoreduction. The disclosed systems achieve desirable results in a broad range of diagnostic, therapeutic and treatment applications, and provide enhanced operating efficiencies and/or processing results in application modalities that employ a broad range of photo-activated and/or photo-responsive materials and/or compounds.

According to the present disclosure, light source(s) are provided that supply light energy having highly advantageous effect(s) on treated fluids, particularly high value and/or complex fluids such as blood products, pharmaceuticals, injectable solutions and vaccines. The present disclosure further provides geometric, spectral, intensity and processing regimens that, when used in conjunction with disclosed light source(s), provide advantageous fluid processing results, both in batch and continuous/semi-continuous treatment systems.

Preferred light source(s) according to the present disclosure supply substantially monochromatic light at high average power outputs, but moderate peak power outputs, thereby reducing or eliminating potential damage to high value/complex fluids due to undesirable heating and/or multi-photon initiated processes. Thus, conventional laser light sources and conventional flash lamps are ineffective/less effective, and are to be avoided according to the systems of the present disclosure. Pulsed laser light sources are undesirable and ineffective according to the present disclosure at least in part due to the high peak power pulses generated thereby. Conventional high intensity lamps, e.g., mercury lamps, fail to provide the wavelength flexibility, processing efficiency, intensity and carrier media preservation, that are critical to treatment systems according to the present disclosure.

It has been found according to the present disclosure that use of the disclosed high output, monochromatic light sources allows effective exploitation of advantageous treatment windows for high value and/or complex fluids, e.g., blood products, pharmaceuticals, injectable solutions and vaccines. Moreover, use of high output, monochromatic light sources as disclosed herein generate synergistic results in complex fluid systems that utilize chemical and/or photoactive agents.

Before describing specific aspects of preferred treatment systems according to the present disclosure, including attributes of preferred light sources and associated apparatus/treatment regimens, a discussion of contemplated fluid treatment applications and/or techniques in which the disclosed treatment systems offer advantageous results is provided. This discussion of exemplary fluid treatment applications and/or techniques is provided at a level of detail that will permit persons of ordinary skill in the art to effectively exploit the innovative treatment systems disclosed herein to achieve advantageous results. Additional fluid treatment applications and/or techniques may also be recognized and/or devised for exploitation of the innovative treatment systems disclosed herein, as will be apparent to persons of ordinary skill in the art from the detailed description that follows, and such additional fluid treatment applications and/or techniques are to be deemed within the scope of the present disclosure.

In a first preferred embodiment of the present disclosure, a system is provided for efficacious treatment of high value/complex fluids that may contain undesirable pathogens, e.g., viral and/or bacterial components, through application of monochromatic light generated by a non-laser light source at advantageous wavelength(s). Exemplary fluids for treatment according to the disclosed treatment regimen include blood products, pharmaceuticals, injectable solutions and vaccines. According to this embodiment, high value/complex fluids are treated to inactivate undesirable pathogens without the addition of chemical additives, photochemical agents and the like, e.g., psoralens, thereby simplifying the treatment regimen and eliminating the need for quenchers and/or post-treatment removal of added materials and/or byproducts.

The disclosed treatment system may be undertaken with respect to high value/complex fluids in real time, i.e., immediately upon the creation and/or availability of the target fluid for treatment. Thus, for example, in the context of blood product or other transfusable/injectable component treatment systems, the disclosed treatment regimen may be advantageously employed immediately upon blood product donation, immediately prior to blood product transfusion, and/or a combination thereof. These processes can include a real time treatment of the blood product as it is moving in the tubing. Alternatively, treatment systems may be deployed to treat high value/complex fluids immediately prior to aseptic packaging, e.g., in large-scale systems for sterilizing solutions prior to packaging thereof. Each of the foregoing treatment systems may be batch, semi-batch, continuous or semi-continuous in operation.

According to preferred embodiments of the disclosed system, substantially monochromatic light energy is delivered to the desired high value/complex fluid to achieve maximal absorbance within or by the target pathogen(s), while simultaneously minimizing damage to the non-pathogenic components and/or substrates, e.g., the carrier media, of the treated fluid. Thus, in the case of blood products, it has been found that particularly desirable pathogen inactivation results may be achieved, without deleterious effect to blood product components within the carrier media, by delivering substantially monochromatic light at a wavelength of between 260 and 310 nm, and generally between 270 nm and 308 nm. Preferred monochromatic wavelengths include 282 nm, 290 nm and 308 nm, although additional wavelengths within the preferred ranges disclosed herein are also deemed to be highly desirable. As used herein, substantially monochromatic light generally exhibits a wavelength distribution wherein the light energy falls predominantly within a range of +/−10 nm relative to the designated wavelength.

Pulsed laser light sources have also been found to affect an unacceptable level of damage to the carrier media. This disclosure notes that the absorption characteristics of biological fluids have a rapid, and surprisingly sharp discontinuity near 300 nm. The change of a few nanometers can have a significant effect. For example, recent measurements of platelets and plasma, demonstrated a change in optical density of greater than 20 times between 270 and 310 nm. (*Photochemistry and Photobiology*, Vol. 71(5) 610-619, 2000) Clearly the processes initiated by the absorption (or transmission) of light on these biological fluids will have a strong wavelength dependence and the term "UV-B" does not adequately define the light source. The light sources disclosed here operating in, but not limited to, narrow bands centered at 259, 282, 290 and 308 nm will each have distinct advantages.

In a further embodiment of the present disclosure, a treatment system is provided in which high value/complex fluids may be treated to reliably and efficaciously inactivate pathogen(s) contained therewithin, wherein the treatment system includes one or more photoactivated compounds and/or additives. Thus, according to the disclosed treatment system, conventional photoactivated compound(s) and/or additive(s) are combined with a treatment fluid, e.g., a blood product, pharmaceutical, injectable solution and/or vaccine, as is known in the art. However, unlike prior art treatment regimens, the disclosed system advantageously irradiates the combined fluid, i.e., high value/complex fluid and photoactivated compound/additive combination, with substantially monochromatic light energy from a non-laser light source at preferred wavelength(s) and intensity(ies), and in preferred geometric/structural arrangement(s), as described in greater detail hereinbelow.

According to the disclosed treatment regimen that includes a conventional photoactive compound/additive, e.g., one or more psoralens, dimethylmethylene blue, riboflavin and the like, pathogen inactivation may be enhanced while minimizing unwanted side effects by irradiating such fluid systems with substantially monochromatic light at wavelength(s) between 270 and 340 nm. Additionally it has been found that small differences in wavelength can have significant effects on cell function, pathogen inactivation, and excitation of photochemical additives. Particularly preferred wavelengths for photochemical additives include 308 nm, 320 nm and 351 nm. For pathogen inactivation, the optimal wavelengths will be 259, 282, 290 and 308 nm. Light delivery to the treatment fluid is controlled such that the wavelength is adjusted and peak intensity levels minimized, thereby advantageously exciting the photoactive compound(s)/additive(s) to achieve the desired results. Thus, in psoralen-based embodiments of the present disclosure, sufficient light intensity is delivered within a narrow spectral range to excite specific adducts. According to such treatment regimens, desirable results are achieved, including inhibiting target pathogen(s) from reproducing/infecting a transfusion recipient, and/or generating improved immune response. Moreover, the systems of the present disclosure provide dose rates that speed these processes.

It is further contemplated according to the present disclosure that particularly advantageous results may be achieved by illuminating/irradiating a fluid system, e.g., a blood system that includes a photoactive compound/additive, so as to achieve the desired activation of the photoactive compound/additive and to additionally effect dissociation of the compound/additive. It is contemplated that the dual processing objectives may be achieved as part of the inactivation process, or in a subsequent monochromatic light-based treatment, e.g., in a continuous processing treatment system. Generation of an optimally effective adduct, e.g., an adduct that is wavelength dependent, or generation of an optimal surface structure that is wavelength dependent facilitates successfully accomplishing both desired results according to the disclosed treatment system.

In another preferred embodiment of the present disclosure, monochromatic light from a non-laser light source is advantageously utilized to effect leukoreduction to minimize or prevent blood platelet alloimmunization, i.e., the transfer of pathogenic immune response information through blood transfusion. Thus, according to a preferred embodiment of the present disclosure, a blood system is treated with monochromatic light having a wavelength at between 260 and 310 nm, generally between 270 and 308 nm, and preferably at a wavelength of 282, 290 or 308 nm. A preferred blood system is treated at an intensity of greater than 20 mW/cm$^2$ to effect desired rates of leukoreduction. Substantially monochromatic light energy having the desired UV-B wavelength is typically generated from a non-laser light source, thereby moderating energy levels in the manner desired according to the disclosed treatment regimen.

It is further contemplated according to the present disclosure that monochromatic light generated by a non-laser light source at predetermined wavelengths will exhibit synergistic effects with different adducts in photophoresis treatment regimens. Thus, it is contemplated that monochromatic light may be used in connection with extracorporeal photophoresis, AIDs treatment, cancer treatment (e.g., cutaneous T cell lymphoma (CTCL)), Lupus treatment, and other disease treatments and/or treatment regimens directed to conditions requiring modulation of the immune system.

Additionally, it is contemplated that graft vs. host disease (GVHD) may be treated through systems utilizing monochromatic light of a predetermined wavelength and intensity.

GVHD treatment regimens may be achieved that optimally inactivate T-cells while preserving other substrates and components to enhance the likelihood of transplant success. In particular, with stem cell transplants, photoactivation with an optimal light energy is believed to maximize inactivation of T-lymphocytes and minimize damage to the hematopoietic stem cells. See Azuma et al. in *Blood* Vol. 96 (7) p. 2632 (2000).

Thus, for example, treatment regimens involving photoactive compounds and/or agents having efficacy in treating the above-noted diseases and/or conditions are believed to exhibit advantageous treatment results when activated with monochromatic light, particularly monochromatic light generated by a non-laser light source, producing "monochromatic" output at discreet wavelengths of between 250 and 400 nm, and preferably 259 to 310 nm.

Additional treatment regimens utilizing substantially monochromatic light are also contemplated according to the present disclosure, including body irradiation techniques and treatment of a variety of medical and health-related fluids. Thus, in a preferred embodiment of the present disclosure, monochromatic light delivery systems are provided that accommodate irradiation of one or more portions of a body, e.g., a limb, extremity or the like. The light delivery system may advantageously permit introduction of the body portion to an enclosed chamber and/or entail paddle light sources that are easily and reliably positioned adjacent the body region to be treated and/or provide faster, more comfortable systems for whole body irradiation. Upon irradiation of the target body region with monochromatic light of a desired wavelength and intensity, photoactivation of the surface layer(s) thereof may be achieved with desirable result. It is noted that systems that produce monochromatic output by selecting a subset of the light sources output using filters, or covert the light sources output to another wavelength using phosphors, or isolate the infrared (heat) of the light sources from the target using fiber optics are limited in size or intensity.

It is additionally contemplated according to the present disclosure that monochromatic light of predetermined wavelength and intensity may be used to advantageously and reliably sterilize fluids, e.g., saline, interperitoneal fluid, vaccines, liquid pharmaceuticals, injectable fluids, and other sterilizable fluids. In particularly preferred embodiments, medical fluids are processed into a relatively thin film and exposed to substantially monochromatic light generated by a non-laser light source at a wavelength between 260 nm and 310 nm to achieve advantageous, uniform dosing. Alternatively, thicker flow streams may be processed, with engineered turbulence to achieve desired uniformity in dosing. Thus, improved sterilization results may be achieved for a range of fluids according to the treatment systems disclosed herein.

It is further contemplated according to the present disclosure that monochromatic light generated by a non-laser light source at predetermined wavelength(s) and intensity(ies) may be utilized to activate/promote chemical synthesis and/or chemical processing. Thus, the activation energy associated with a specific process step and/or the kinetic parameters associated with a particular chemical process may be supplied by such monochromatic light, thereby potentially boosting yields and speeding process rates. For example, processes that are biologic in nature, e.g., activation/inactivation of biologic organisms influencing chemical processes, or chemical in nature, e.g., dependent upon the excitation of specific active site(s) and/or functional group(s), may be promoted and/or enhanced through monochromatic light energy supplied according to the present disclosure.

In all cases, dose determination is not straightforward in opaque fluids. Previous disclosures have often mistaken surface dose with dose delivered to the fluid volume. The large area sources disclosed herein allow dose to be advantageously controlled through changes/modifications in light source geometry. Typical systems require severe overdosing at some volumes to ensure adequate dosing of others. The disclosed treatment systems, however, provide a means to treat complex, opaque fluid volumes more uniformly. Additional analysis can identify wavelengths where absorption is minimized and scatter is maximized—this will produce a peaked intensity profile within the fluid. The thickness of the fluid can therefore be engineered to enable more uniform dosing. In some cases, the use of light scattering, may achieve dose distributions similar to two sided excitation, but with one sided excitation.

In short, substantially monochromatic light having predetermined wavelength, geometry and intensity characteristics may be exploited to achieve and/or deliver significant benefits in a wide range of applications, systems and techniques according to the present disclosure. Through control of the wavelength, intensity and delivery characteristics of the monochromatic light, advantageous results are achieved in a plurality of fluid applications, with a high degree of specificity and in an economically desirable manner. Having thus described a series of applications and techniques that may advantageously exploit monochromatic light of predetermined wavelength, attention is now turned to preferred systems for generating and delivering monochromatic light to treatment fluids according to the present disclosure.

With reference to FIGS. 1 and 2, a treatment apparatus 100 is depicted for advantageously treating high value/complex fluids according to the present disclosure. Treatment apparatus 100 is configured and dimensioned to receive an advantageous light source for generating substantially monochromatic light according to the present disclosure, and is configured to treat high value/complex fluids positioned external thereto, e.g., blood products, in batch or semi-batch treatment regimens. Treatment apparatus 100 is merely exemplary of preferred treatment apparatus according to the present disclosure, as will be apparent from the discussion that follows.

Treatment apparatus 100 includes a housing 102, an inlet port 106 adjacent a first end of housing 102, and an outlet port 104 adjacent an opposite end of housing 102. Housing 102 includes an outer wall 103 that defines a substantially square cross section. End flanges 107a, 107b are provided at either end, each end flange 107a, 107b defining a substantially circular surface 109 that bounds an opening 110. Flanges 107a, 107b are typically welded to outer wall 103 to define a fluid-tight volume 105 (with an inserted light source, as described below) which is in fluid communication with inlet and outlet ports 104, 106.

Outer wall 103 and the inner faces of end flanges 107a, 107b may be advantageously fabricated from, or surface treated with, a reflective material, e.g., aluminum. Such reflectivity assists in directing ultraviolet radiation toward high value/complex fluids being treated by apparatus 100, as described hereinbelow. Outer wall 103 and end flanges 107a, 107b may be fabricated from a relatively rigid material having sufficient strength to withstand the fluid pressure and fluid flow within volume 105. Aluminum is a preferred material for use in fabricating outer wall 103 and end flanges 107a, 107b, although other metals are also contemplated.

In a preferred embodiment of the present disclosure, housing 102 functions as a ground for a light source positioned within volume 105. In such instance, outer wall 103 of housing 102 is necessarily fabricated from a conductive material, e.g., aluminum, and is electrically grounded, as is known in the art. The importance of the grounding properties of housing 102 to advantageous operation of preferred systems according to the present disclosure will become more readily apparent from the light source discussions which follow.

Inlet and outlet ports 106, 104 advantageously communicate with a source of cooling fluid (not pictured), preferably a cooling fluid that is substantially transparent to ultraviolet radiation. For example, inlet port 106 may be connected to a source of cooling water that advantageously flows through volume 105, and exits housing 102 through outlet port 104. Cooling water may be advantageously recycled to housing 102 and/or passed through a light source (either before or after passage through volume 105), as described in greater detail hereinbelow. The flow rate of the cooling fluid within volume 105 is controlled through conventional means, e.g., valving, available water pressure and/or pump settings.

A quartz plate 108 is centrally mounted on one face of housing 102 by mounting flange 112 to facilitate passage of light energy from a light source (not pictured in FIGS. 1 and 2) positioned within circular passage 110 to high value/complex fluids positioned external thereto. Quartz plate 108 is advantageously defined by three individual quartz panels 108a, 108b, 108c to provide a desired level of light energy transmission from housing 102 for treatment of high value/complex fluids positioned adjacent quartz plate 108. Cross beams 112a that separate quartz panels 108a, 108b, 108c from one another advantageously provide additional grounding to a light source positioned within housing 102, as described below. The external surfaces of quartz panels 108a, 108b, 108c define treatment surfaces upon which, or in substantial juxtaposition with which, high value/complex fluids may be treated according to the present disclosure. By placing the high value/complex fluid in direct contact with quartz plate 108, minimal reflection of the monochromatic light delivered through cooling fluid-containing volume 105 and quartz panels 108a, 108b, 108c is permitted.

Of note, high value/complex fluids, e.g., blood products, may be positioned on the external surfaces of quartz panels 108a, 108b, 108c within storage vessel(s) or container(s), e.g., treatment bag(s), that are highly transparent to ultraviolet radiation, e.g., flexible bags fabricated from poly (ethylenevinyl acetate), as are known in the art. The storage vessel/container is preferably free of leachable materials. The high value/complex fluids within the storage vessels/containers are advantageously substantially flattened to define a relatively uniform fluid depth or thickness to be treated according to the present disclosure. Mixing of the complex fluid may be provided through appropriate mechanical means, if desired, during irradiation treatment. Transfusion Medicine 7(1) 1 (1993) and Transfusion 30 p 678 (1990).

According to preferred treatment systems according to the present disclosure, a non-laser light source is introduced through opening 110 in flanges 107a, 107b for treatment of high value/complex fluids positioned adjacent or in juxtaposition with quartz panels 108a, 108b, 108c.

With reference to FIG. 3, exemplary non-laser light source 200 is schematically depicted in cross section. Light source 200 is substantially cylindrical in geometry and is advantageously configured and dimensioned for introduction into opening 110 of housing 102. Light source 200 advantageously rests on circular surfaces 109, thereby centering light source 200 within housing 102 and defining a fluid-tight volume 105. The ability to introduce and withdraw light source(s) from housing 102 is clearly advantageous in numerous respects, including an enhanced ability to service light source(s), as needed, and increased flexibility in utilizing alternative light source(s) within housing 102, e.g., to generate substantially monochromatic light energy of varying wavelengths. Alternatively, a light source may be integrally associated with housing 102, i.e., non-removable with respect thereto. In such case, it is contemplated that the photon-producing gas(es) contained within the light source may be replaceable/substitutable. Thus, in either case, apparatus 100 provides significant versatility in the treatment of high value/complex fluids with light energy of varying wavelengths.

Monochromatic light source 200 includes an outer wall 202 and an inner wall 204 that cooperate to define an annulus 206. An elongated conductor 208 extends the length of light source 200, preferably along the central axis of the light source's cylindrical geometry. A substantially cylindrical region 210 is defined between inner wall 204 and elongated conductor 208. Cylindrical region 210 advantageously communicates with inlet and outlet ports for ingress and egress of cooling fluid, e.g., cooling water. End flanges are provided to define fluid tight seals for annulus 206 and cylindrical region 210. Thus, monochromatic light source 200 generally includes three elongated, concentric elements: elongated conductor 208, cylindrical region 210 and annulus 206.

According to the present disclosure, light emitting, i.e., photon-producing, gas sources are contained within the bounded volume of annulus 206. Preferred light emitting/photon-producing gas sources are "excimers," as are known in the art. Excimer sources (also called "excited dimers") driven by dielectric barrier discharge offer a unique, advantageous set of capabilities for fluid treatment regimens according to the present disclosure: operation at ambient temperature, discretely tunable monochromatic output, variable emitting areas, and high germicidal UV output per lamp. Dielectric barrier discharge technology is known for its ability to produce energetic molecular species at ambient temperature discharge and is also used to generate ozone. Applicable voltages, frequencies and currents are known to those of ordinary skill in the art. This excitation source allows even high power excimer lamps to operate at the same temperature as the fluid to be treated based on the advantageous geometric/structural arrangements disclosed herein. As described herein, excimer sources may also be built in a variety of advantageous geometric configurations. Because the light generating electrical discharge occurs, not as a single large arc, but as a large number of short arcs distributed over a large area, excimers are especially well suited as large area emitters. Similarly, since the light producing discharge is independent of the size and shape of the lamp, excimers can be used to produce surface emitters of unusual, and useful, shapes.

Monochromatic light source 200 emits light uniformly over its entire surface area and is configured to operate at reduced temperatures, particularly based on the system designs disclosed herein. The substantially monochromatic output of light source 200 can be tuned to produce high spectral irradiance (watts/nm) within peaks of the process action spectra to maximize the effectiveness of the light energy, e.g., for pathogen inactivation, leukoreduction, and the like. Excimer sources advantageously produce light output wherein 90% of the output is within a 10 nm band, and preferably a 5 nm bandwidth. The light output may be discretely adjusted across VUV, UV-A, UV-B and UV-C wavelength regions by changing the rare and/or halogen gases used. Efficiencies vary with gas mix and geometry from 10% to greater than 30% efficiency, with demonstrated input powers from less than one watt to greater than 10 kW.

According to the present disclosure, it has been found that monochromatic light emission is required to optimally process most fluids due to the wavelength-specific absorbence characteristics of the fluid, the preservation of critical fluid functions, and/or the efficient delivery of light to produce a desired effect. An irradiation device where the emitting surface of the irradiator is both temperature controlled and in contact with the target is highly desirable. In this way, the unit efficiently delivers light, and controls the temperature of the sample. This can also be viewed as monochromatic emission since heat energy is infrared radiation. For the treatment of fluids with a high scattering coefficient system parameters can be optimized to control the sub-surface intensity peak which is produced by back scattered light. This peak is best produced when the light is delivered to the fluid with a matched refractive index. To do this ideally there is not an air gap between the lamp and the target fluid—the fluid must be in contact with the lamp surface. In the ideal configuration, back scattered photons produce a discreet area of high intensity—essentially using each photon several times to minimize the size and power of the required light source.

Shorter wavelengths, it is understood, damage the blood component. Less appreciated is that longer wavelengths can result in repair of inactivated organisms in a disinfection process, unintended byproduct formation when chemical additives are used and, in all cases, heating by infrared emissions.

Higher intensity sources generally result in faster processing times. However, very intense light sources, like lasers and flash lamps, can also generate non-linear effects including surface ablation and "two-photon excitation." Therefore, for all first order processes, defined here as processes that are dependent on dose and/or the number of absorbed photons, a continuous-duty light source as disclosed herein provides optimal dose rates, while minimizing unwanted effects due to high intensity. High average power is therefore preferred because it speeds process times.

According to the present disclosure, excimer light sources may be provided to deliver a variety of wavelengths based on the gas(es) utilized. Preferred excimer light sources/gas (es) are summarized in Table 1.

TABLE 1

| Excimer Gas(es) | Wavelength |
|---|---|
| XeI | 253 |
| $Cl_2$ | 259 |
| XeBr | 282 |
| $Br_2$ | 289 |
| XeCl | 308 |
| Filtered XeBr | 320 |
| $I_2$ | 342 |
| XeF | 351 |

With reference to FIG. 4, light source 200 is typically positioned within apparatus 100 by sliding light source 200 through opening 110. Cooling fluid is typically supplied to cylindrical region 210, e.g., cooling water from a conventional source. Of note, cooling fluid may be supplied in series to apparatus 100 and light source 200. Such cooling fluid may be supplied first to apparatus 100 or to light source 200, and may flow co-currently or countercurrently within the respective fluid-tight regions. Treatment fluid 250 is bounded by vessel 252, e.g., a blood bag or tube and positioned adjacent to or in juxtaposition with quartz panels 108a, 108b, 108c within flange 112, i.e., external to housing 102. In a preferred embodiment of the present disclosure, the treatment fluid is a blood product, pharmaceutical, injectable solution or a vaccine.

Light source 200 is energized to deliver monochromatic light energy by supplying alternating voltage to elongated conductor 208 and establishing housing 102 as a ground for the overall system. Voltage supplied to elongated conductor 208 typically falls within a range of 100 to 10,000 volts. The capacitive coupling between the high voltage within elongated conductor 208 and grounded housing 102 excites the photon-producing excimer gas(es) contained within the bounded volume of annulus 206. Based on the excimer gas(es) contained within annulus 206, substantially monochromatic light of a substantially uniform wavelength is generated and delivered from annulus 206, i.e., across substantially the entire surface area of outer wall 202 and inner wall 204. The monochromatic light energy is advantageously transmitted through the cooling fluid contained within volume 105 and quartz plate 108 to treat the treatment fluid 250 within vessel 252 that is positioned adjacent to or in juxtaposition with quartz panel 108. The internal reflectivity of housing 102, if any, contributes to maximizing the amount of monochromatic light that is transmitted through quartz plate 108 for treatment of treatment fluid 250. In addition, reflector(s) may be added to increase flux through quartz plate 108.

In preferred embodiments of the present disclosure, light source 200 contains excimer gas(es) selected from those set forth in Table 1 hereinabove. Treatment fluid 250 is advantageously selected from among blood products, pharmaceuticals, injectable solutions and vaccines, although it is further contemplated that other fluids may be treated according to the present disclosure, as described hereinabove. It is further contemplated that treatment fluids positioned adjacent to, or in juxtaposition with, quartz plate 108 may contain photoactive compounds and/or materials, e.g., psoralens and the like, that are activated or otherwise affected by the monochromatic light delivered by light source 200.

Preferred treatment parameters vary depending on several factors, including the characteristics of the fluid being treated, the desired outcome of the treatment, and the wavelength of the monochromatic light being transmitted by light source 200. However, it is generally contemplated that fluid treatments according to the present disclosure will involve delivery of monochromatic light having a wavelength of between 250 and 400 nm; for pathogen inactivation preferably between 260 and 310 nm; and for chemical excitation preferably from 220 to 350 nm. The monochromatic light treatment typically involves surface dosages of 0.1 to 10 $J/cm^2$, based upon intensities of 2 to 50 $mW/cm^2$ and treatment times of 5 seconds to 15 minutes.

Several unique advantages are apparent from the fluid treatment regimens described herein. Given the susceptibility of treatment fluids to undesirable heating during treatment, the advantageous continuous cooling of the treatment fluids by cooling fluid within volume 105 prevents deleterious effects to the treatment fluids during treatment with monochromatic light according to the present disclosure. Beyond cooling, "cooling fluid" that flows through volume 105 may be used to control the temperature of the treatment fluid at any desired temperature level, depending on the requirements of the treatment system. Thus, it is contemplated that the "cooling fluid" may be used to heat and/or moderate the temperature of the treatment fluid, as desired by users of the disclosed system. Moreover, cooling fluid flowing within cylindrical region 210 advantageously facilitates efficient cooling of light source 200.

Thus, unique aspects of the monochromatic light generation system according to the present disclosure, wherein an excimer light source is positioned within a fluid-tight, cooling fluid volume, permit reliable and efficacious cooling (or temperature moderation/control) of a treatment fluid through direct heat transfer between the treatment fluid and a substantial heat sink in close proximity thereto. Indeed, according to the present disclosure, it is possible to ensure negligible heat gains and/or temperature change within a treatment fluid throughout the duration of a treatment regimen. The transmission characteristics of water permit operation of this design with a wide range of wavelengths.

In addition, monochromatic light energy within the desired UV wavelength ranges that is delivered to treatment fluids according to the present disclosure is advantageously generated and transmitted across a substantial surface area, the geometry of which advantageously conforms or corresponds to the surface area geometry of the treatment fluid. Thus, unlike conventional high intensity bulbs and/or elongated fluorescent light generation apparatus, which generate light from a "point" or "linear" source, the disclosed treatment system advantageously generates monochromatic light through a surface. The shape of this light emitting surface is directly associated with the fluid-tight enclosure/housing, e.g., mounted thereto. In the disclosed embodiment of FIGS. 1-4, the light emitting surface geometry is defined by quartz panel 108 and is substantially planar. The geometry of the treatment surface of the treatment fluid 250 substantially conforms or corresponds to such planar emitting surface, i.e., the treatment surface geometry is also substantially planar. The advantageous relationship between the light emitting surface geometry and the fluid treatment surface geometry translates into reliable and efficacious energy delivery to the treatment fluid.

Thus, according to the present disclosure, light source(s) for fluid or surface treatment are advantageously provided wherein the surface area geometry of light source emission conforms/corresponds to the surface area geometry of the fluid and/or fluid container to be treated. Surface emitter sources that emit uniformly across a large area can be placed close to the target—providing a very small footprint, high intensities, and a uniform irradiation field. While a planar arrangement as depicted in FIGS. 1-4 provides efficient energy delivery to the treatment fluid, it is contemplated that the fluid container may be a tube, where the light source is an annulus irradiating inwardly. The container may also be a thin sheet, in which case the light source is a plane. The container may be a bag, in which case the light source may be a hollow volume, approximating the shape of the bag (similar to a mold) which radiates inwardly. The container may also be an annulus, in which case the light source may be a cylinder radiating outwardly, or an annulus (of large diameter) radiating inwardly. In all cases, the surface area of the light source is engineered to match the fluid container, providing a more uniform dose distribution to the treated volume. For photodynamic therapies (PDT), the concept of "vessel" or container for the treatment fluid can be extended to include the human body or a limb of the body, for whole body irradiation or skin treatment. Hence, light sources that are surface emitters, as disclosed herein, rather than point sources or linear sources, offer significant treatment advantages for high value/complex fluids, as described herein.

While preferred systems according to the present disclosure have been described in some detail with reference to the embodiments of FIGS. 1-4, a range of alternative structural and geometric arrangements for delivering substantially monochromatic light energy are contemplated. For example, as shown schematically in FIGS. 5 and 6, apparatus 300 may be utilized to generate and deliver monochromatic light from a light source 350. Light source 350 includes an annulus 360 within which excimer gas is contained. Alternating voltage is supplied to a conductive screen 370 positioned adjacent an inner wall 365 of annulus 360, and a housing (not pictured) that may advantageously surround light source 350 typically provides a ground with respect thereto. Housing 350 may also function as a reflector to direct light energy inward. A fluid-tight annulus 330 is provided interior of excimer gas-containing annulus 360. A cooling fluid typically flows within fluid-tight annulus, e.g., cooling water or air. Treatment fluid 380 to be treated by apparatus 300 typically flows through central tubular region 390. Tubular region 390 may be an integral component of apparatus 300, or may be defined by tubing that is introduced to and/or threaded through along the central axis of apparatus 300, e.g., as blood is obtained from or transfused to an individual. Tubing may be advantageously fabricated from Teflon or the like.

A modification of this device uses the treatment fluid as a capacitive media to couple power to the gas mixture. This eliminates the need for screens. (See FIG. 3 as a representative example)

Fluid to be treated by apparatus 300 may be selected from among blood products, pharmaceuticals, injectable solutions, vaccines and other fluid systems. Cooling fluid within cooling annulus 330 advantageously provides immediate cooling (or temperature control/moderation) of treatment fluid 380 passing through tubular region 390, thereby ensuring that undesirable temperature changes do not damage or negatively impact the treatment fluid 380. Moreover, monochromatic light is generated and inwardly transmitted toward treatment fluid 380 across a substantial surface area, i.e., the surface area of inner wall 365. The light emitting surface area geometry across which monochromatic light is transmitted to treatment fluid 380 conforms or corresponds to the treatment surface geometry for treatment fluid 380 as it passes through central tubular region 390, i.e., an annular surface geometry. This system design (FIGS. 5 and 6) has particular advantages for transfused blood products where handling of the fluid is to be minimized and tubing is already used to transport fluid from donor to storage to recipient.

With reference to FIG. 7, a cross section side view of a further alternative treatment system according to the present disclosure is depicted. Apparatus 700 includes a symmetric pair of photon-emitting excimer light sources 702a, 702b, each enclosed within a housing defined by an inner wall 704 and an outer wall 706. The external walls 708 of apparatus 700 are grounded at grounds 710a and 710b. A screen 712 is provided adjacent to, but internal of, inner wall 704. A treatment fluid 720 is contained within a vessel 722. A fluid-tight region 724 separates vessel 722 from inner wall 704 of light sources 702a, 702b. A cooling fluid and/or gas is generally located within region 724. The cooling fluid/gas may be statically contained within region 724 or may flow therethrough, to provide a desired level of temperature control/moderation. This design has particular applicability to extracorporeal photophoresis systems, or flow through pathogen inactivation process.

In use, alternating voltage is delivered to screen 712. The voltage generated between screen 712 and ground 710 excites the excimer gas(es) contained within light sources 702a, 702b. Alternating voltage may be applied between grounds 710a and 710b to excite both light sources 702a, 702b from a single power supply. Monochromatic light is generated and delivered through inner wall 704, the cooling fluid/gas contained within fluid-tight region 724, and vessel 722 so as to treat fluid 720 contained therein. The light emitting surface geometry conforms/corresponds to the treatment geometry, i.e., both are substantially planar. Moreover, cooling fluid/gas within region 724 provides advantageous temperature control/moderation to treatment fluid 720 throughout the treatment regimen. Of note, apparatus 700 may be of a relatively large scale and may operate as light emitting paddles or as radiating walls for an enclosure for use in whole body and/or limb monochromatic light treatments. An alternate view of the device is shown in FIGS. 11a and 11b. As shown in these figures, the fluid to be treated proceeds along the path identified by flow arrow "F". Gas is contained within region 920 and power source 930 is electrically connected to electrodes 910. An alternating voltage is delivered to electrodes 910. The specific design points (intensity, total power, area, etc) can be determined for this device for a target flow using the algorithm also shown in FIG. 10.

With reference to FIG. 8, apparatus 800 is schematically depicted according to the present disclosure. Apparatus 800 includes a substantially elliptical annulus 802 that contains excimer gases for monochromatic light generation and emission. A substantially elliptical high voltage screen 804 is positioned within annulus 802 within a fluid-tight region 806. A treatment fluid 808 is positioned centrally to apparatus 800 within a container 810 that defines a substantially elliptical outer geometry. Container 810 may be a blood bag or the like. The outer housing of apparatus 800 is grounded (not pictured) to allow excitation of the excimer gases within annulus 802 upon delivery of high voltage to screen 804. Fluid-tight region 806 advantageously contains a cooling fluid/gas to control/moderate the temperature of treatment fluid 808 throughout the treatment thereof. The light emission surface area geometry (substantially elliptical) advantageously conforms to the treatment surface defined by container 810 (substantially elliptical).

As is readily apparent from the preceding description, an elliptical design is merely exemplary of a non-symmetric geometric design contemplated according to the present disclosure. However, such elliptical design is not to be deemed limiting of the scope of the present disclosure, and it is to be understood that other non-symmetric geometric designs are contemplated and offer potential advantages to various treatment regimens.

As with most treatment fluids, in treating blood products the light source must be configured to operate reliably and economically. Blood products are opaque, i.e., they absorb and scatter light over small distances. Blood is also a delicate fluid requiring temperature control and gentle mechanical handling. Blood bags are optimized for the safe and stable storage of blood products, for optimal handling, and to minimize potential contamination, not for efficient irradiation. Based on inherent limitations associated with blood bags and other blood containers, it would be highly desirable to treat blood products before they enter storage bags in the first instance or upon egress therefrom. In other words, it is highly desirable to provide an irradiation device for blood products that accommodates real time treatment of flowing blood.

A preferred embodiment for providing real time treatment of flowing blood according to the present disclosure utilizes a light source that provides a targeted dose to blood flowing in a tube, e.g., utilizing apparatus 300 of FIGS. 5 and 6, to blood flowing in a sheet or plane, e.g., as shown in FIG. 7, or similar system designs. Several design points are used to optimize preferred systems according to the present disclosure. First, as with any opaque fluid, light intensity varies greatly over small distances as light is absorbed (and scattered) by the fluid. Delivery of a uniform dose usually requires thin films. The use of optimized light emitting surfaces will have advantages for treating cylindrical flows that minimize the dose distribution that complicates treatment of thin films, including the balancing effects of absorbence and converging light.

While light intensity drops off with distance as a function of absorbence, following Beer's law, dose is dependent on intensity. Therefore, dose is dependent on the thickness of the fluid sample. Over-exposure of some target material may be required to adequately dose another part of the target. Since turbulence can damage blood products, opportunities to use mixing are generally limited. Thin films have therefore been used in an effort to deliver a more uniform dose. This may not be optimal. For certain fluids at certain wavelengths the light system can be designed to maximize back scattered light. A specific example is the use of 308 nm light and platelets or plasma where light propagation is dominated by scatter. In addition to geometric issues, dose is time dependent. Flow can be optimized to minimize dose range. This is not easily achieved with blood products.

In this regard and with reference to apparatus 300 depicted in FIGS. 5 and 6, it is noteworthy that central tubular region 390 may receive treatment fluid directly, or in an alternative embodiment, central tubular region 390 may receive a tube or pipe threaded therethrough. Thus, for example, in blood donation and/or blood transfusion systems, tubing passing to or from a patient's body may pass through tubular region 390, thereby permitting the blood stream to be treated with monochromatic light from light source 350 in real time, i.e., in the process of blood donation and/or in the process of blood transfusion to a recipient. Such blood streams receive immediate and continuous cooling from cooling fluid that passes through cooling annulus 330.

Inasmuch as annulus 360 (which contains the excimer gas) surrounds tubular region 390 in apparatus 300 of FIGS. 5 and 6, light source 350 advantageously simultaneously delivers monochromatic light to a treatment fluid within tubular region 390 from all directions. The structural and geometric arrangement thus optimizes light intensity distribution to the treated fluid, by transmitting light energy inwardly from an annular light transmission surface. The flow of the treatment fluid through tubular region 390 may also be substantially non-turbulent, thereby minimizing the potential damage to treatment fluids passing therethrough. It is envisioned that a device without a screen similar to FIG. 11 can be used where the electrical power is coupled through the treated fluid. The device can be non-cylindrical in configuration, as illustrated in FIGS. 7 and 8 or planar as detailed in FIG. 11.

Transfer tubes thus offer an advantageous geometric opportunity because light transmission reaches the treatment fluid from multiple directions simultaneously. A tube irradiated from all sides can have a near optimal uniform dose distribution. Since the proposed light source delivers a uniform intensity to the entire surface area of the tube. While light is absorbed as it travels toward the center of the tube, this effect is opposed by the smaller effective area the light flux must pass through. Total optimization, considering both the absorbance and scattering components of the fluids optical density, may require only an adjustment of the tube diameter, as is well within the skill of persons skilled in the art.

Beyond the inward irradiation systems disclosed in FIGS. 5-8, it is further contemplated that the fluid flow may be through an annulus surrounding the excimer gas. In this alternative embodiment, monochromatic light would be radiating both outwardly and inwardly through the treatment fluid, with many of the benefits of apparatus 300 disclosed hereinabove, e.g., real time treatment, reliable cooling, etc. Of note, in apparatus 300 and other flow designs according to the present disclosure, it is contemplated that treated fluid may be recycled (in whole or in part) and/or fed to further treatment apparatus aligned in series for further processing, as may be needed to achieve the desired treatment results. Indeed, it is contemplated that a series of treatment apparatus may be arranged in series, with multiple light sources introducing light energies of differing intensities and/or wavelengths to respective treatment apparatus, thereby expanding the treatment regimen to target different pathogens and the like.

Thus, treatment apparatus according to the present disclosure are not limited to the exemplary designs shown in the accompanying figures, but may take a variety of geometric forms and structural arrangements, as will be apparent to persons skilled in the art based on the detailed description provided herein. Alternative treatment apparatus may thus be utilized, provided the desired monochromatic light irradiates the treatment fluid for a time and to a degree necessary to achieve the desired results, without imparting undesirable heating of the treatment fluid.

To further illustrate advantageous applications of the disclosed treatment systems, several examples are provided that illustrate certain specific aspects of the present disclosure. However, it is to be understood that these examples are merely exemplary of applications, techniques, systems, methods and apparatus utilizing the disclosed technology, and are not to be limitative thereof. Many variations and alternative applications of the disclosed technology that fall within the spirit and scope of the present disclosure are contemplated and will be apparent to those of skill in the art from the detailed description provided herein, and the examples that follow.

EXAMPLE 1

As depicted in FIGS. 1-4, apparatus 100 was utilized with light source 200 positioned therewithin to simulate processing of blood products using a photochemically activated process. XeBr was selected as the excimer gas. The output was filtered using window glass to remove 282 nm light and pass only the emission centered at 320 nm. Blood products contained within conventional blood bags were positioned atop quartz plate 108 and irradiated with monochromatic light from the XeBr excimer light source. Cooling fluid flowing through the treatment apparatus maintained the blood samples at a constant temperature, and prevented any deleterious effect thereto. Platelets were maintained at 24° C., based on the cooling fluid being supplied to the system at that temperature and the platelet bag being in intimate contact with the relatively large surface area of the quartz panels.

Based on irradiations with the XeBr excimer source using the apparatus of FIGS. 1-4, no clinically significant effect on platelets was observed for exposures greater than 4 $J/cm^2$ measured as a change in platelet count (immediately after irradiation or 24 hours later), CD62, morphology score, LDH, pH, pO2, PCO2 or bicarbonate, osmatoc recovery. Similarly for plasma irradiations >4 $J/cm^2$ showed no effect on PT<PTT, fibrogen or Factor VIII. For red cells, measurements included hematocrit, LDFH, 2,3 D-P-G, % hemolysis and others. No changes were observed with surface doses greater than 4 $J/cm^2$.

Based on these test results, it was concluded that the disclosed treatment system was effective in treating blood product samples without causing deleterious effects thereto a shown in tables 2 and 3 and again in FIGS. 12 and 13.

EXAMPLE 2

These experimental studies were designed to show that refractory viral contaminants can be inactivated using 282 nm light in real blood products using the treatment systems of the present disclosure. The system was evaluated for its ability to inactivate porcine parvovirus (PPV). PPV (NADL-2 strain) is an 18-26 nm, non-enveloped, DNA-containing parvovirus, which exhibits a high degree of resistance to a range of physico-chemical reagents. It is not treated using cell washing techniques because it is non-enveloped. PPV inactivation using psoralen and riboflavin are inefficient because the small genome size of the virus requires either larger doses of activating compound or longer irradiation times.

The strength (titer) of the production lot of virus used in the study was determined by a plaque assay utilizing ST indicator cells. GLP lab standards were maintained. The PPV stock solution used in this example tested positive for identity when tested with a polyclonal antisera specific for PPV and is free of potential bovine (BAV, BPI3, BPV, BVDV, IBR, and REO-3) and porcine (PAV and TGE) viral contaminants.

The blood components were not diluted, and were treated as they would be stored in a blood bank. Volumes used (30 to 150 ml) and the size of bags simulated the thickness of blood product in standard storage bags. Samples which altered the virus titers by >0.5 $\log_{10}$ were considered to interfere. If the samples showed significant levels of interference, the results were reviewed prior to proceeding. PPV titers measured as PFU/mL were reduced by >5 logs for both Fresh Frozen Plasma and Platelets as shown in chart #5.

Fresh Frozen Plasma

Three units of fresh frozen plasma (FFP, approximately 300 mL/unit) were pooled. The pooled mixture was then spiked with 1% of PPV stock solution (exact volumes were recorded at the time of spiking). The spiked starting materials were then divided into three, 100 mL samples and ten, 50 mL samples.

A 6 mL sample of the spiked starting material was removed from one of the 100 mL aliquots, adjusted to pH 6.5-7.5 (if necessary) and divided into multiple aliquots. One aliquot was tested immediately, the remaining aliquots were snap frozen, and stored as backups at or below −70° C. The remaining 94 mL of sample was held at ambient temperature for the duration of the process. Following incubation, a 6 mL sample was removed, adjusted to pH 6.5-7.5 (if necessary) and divided into multiple aliquots. One aliquot was tested immediately, the remaining aliquots were snap frozen, and stored as backups at or below −70° C. The remaining spiked samples were then treated with 282 nm monochromatic light in the apparatus of FIGS. 1-4.

Following treatment, a 6 mL aliquot was removed from each treated sample, adjusted to pH 6.5-7.5 (if necessary) and divided into multiple aliquots. One aliquot was tested immediately, the remaining aliquots were snap frozen and stored as backups at or below −70° C.

Platelets, RPC

Six units of random platelet concentrates (RPC, approximately 65 mL/unit) were pooled. The pooled mixture was then spiked with 1% of PPV stock solution (exact volumes were recorded at the time of spiking). The spiked material was then divided into three, 60 mL samples and seven, 20 mL samples. A 6 mL sample of the spiked starting material was removed from one of the 60 mL aliquots, adjusted to pH 6.5-7.5 (if necessary) and divided into multiple aliquots. One aliquot was tested immediately, the remaining aliquots were snap frozen, and stored as backups at or below −70° C. The remaining 54 mL of sample was held at ambient temperature for the duration of the process. Following incubation, a 6 mL sample was removed, adjusted to pH 6.5-7.5 (if necessary) and divided into multiple aliquots. One aliquot was tested immediately, the remaining aliquots were snap frozen, and stored as backups at or below −70° C. The remaining spiked samples were then treated with 282 nm monochromatic light in the apparatus of FIGS. 1-4.

Following treatment, a 6 mL aliquot was removed from each treated sample, adjusted to pH 6.5-7.5 (if necessary) and divided into multiple aliquots. One aliquot was tested immediately, the remaining aliquots were snap frozen, and stored as backups at or below −70° C.

Results

For both platelets and plasma, the PPV was reduced to non-detectable levels. The maximum log removal shown is that which could be quantified given the limits of detection. Extra wells were set for the highest dose measurements, and no virus was detected.

Test results are reflected in the following Tables.

TABLE 2

Log$_{10}$ Reduction Summary - Fresh Frozen Plasma

| Virus | Sample/Volume/Surface Dose/Notes | Log$_{10}$ Reduction |
|---|---|---|
| PPV | FFP/100 mL/4 J/cm$^2$/Mixed | 2.24 ± 0.18 |
| | FFP/100 mL/8 J/cm$^2$/Mixed | 3.14 ± 0.16 |
| | FFP/50 mL/1 J/cm$^2$/Mixed | 1.27 ± 0.13 |
| | FFP/50 mL/2 J/cm$^2$/Not mixed | 0.97 ± 0.27 |
| | FFP/50 mL/2 J/cm$^2$/Mixed | 2.03 ± 0.24 |
| | FFP/50 mL/4 J/cm$^2$/Not mixed | 1.02 ± 0.18 |
| | FFP/50 mL/4 J/cm$^2$/Mixed | 2.04 ± 0.25 |
| | FFP/50 mL/8 J/cm$^2$/Not mixed | 1.34 ± 0.13 |
| | FFP/50 mL/8 J/cm$^2$/Mixed | 4.24 ± 0.25 |
| | FFP/50 mL/16 J/cm$^2$/Not mixed | 2.47 ± 0.22 |
| | FFP/50 mL/16 J/cm$^2$/Mixed | * >4.87 ± 0.12 |
| | FFP/50 mL/32 J/cm$^2$/Mixed | * >4.87 ± 0.12 |

* Virus reduced to non-detectable levels.

TABLE 3

Log$_{10}$ Reduction Summary - Random Platelet Concentrates

| Virus | Sample/Volume/Surface Dose/Notes | Log$_{10}$ Reduction |
|---|---|---|
| PPV | RPC/60 mL/4 J/cm$^2$/Mixed | 2.35 ± 0.21 |
| | RPC/60 mL/8 J/cm$^2$/Mixed | 4.14 ± 0.21 |
| | RPC/20 mL/1 J/cm$^2$/Mixed | 1.43 ± 0.31 |
| | RPC/20 mL/2 J/cm$^2$/Mixed | 2.42 ± 0.36 |
| | RPC/20 mL/4 J/cm$^2$/Mixed | 4.90 ± 0.19 |
| | RPC/20 mL/8 J/cm$^2$/Not mixed | 2.95 ± 0.19 |
| | RPC/20 mL/8 J/cm$^2$/Mixed | * >5.93 ± 0.16 |
| | RPC/20 mL/16 J/cm$^2$/Not mixed | 4.45 ± 0.19 |
| | RPC/20 mL/16 J/cm$^2$/Mixed | * >5.93 ± 0.16 |

* Virus reduced to non-detectable levels.

Based on the foregoing test results, it is clear that substantially monochromatic light at a wavelength of 282 nm delivered in the disclosed treatment system is effective against porcine parvo virus in both plasma and platelets.

EXAMPLE 3

In order to establish the effectiveness of longer wavelength light produced by the XeBr source, tests were made comparing inactivation rates at 282 nm to those measured at 260 nm. 260 nm is near the peak of the germicidal action spectra. Monochromatic light is produced using an excimer lamp using $Cl_2$ to produce light at comparable intensities at 260 nm. A lab cultured *coli* was used.

A collimated beam apparatus was used to deliver light to static sample containers. Heterotrophic plates counts (HPC) were performed as per Standard Methods Spread Plate Method (9215 C.) (19$^{th}$ Ed). This included serial diluting the sample by 10 s using 50% Difco nutrient broth as diluent, pipetting 100 μL of each dilution onto the plates, and spreading the sample with a plastic disposable spreader so that the entire sample is absorbed into the agar media. Samples were incubated (plates inverted) at 32-35° C. and counted for quantification of heterotrophic bacteria at 24 hours and again at 48 hours and recorded. Only the analytical plate (that with colonies between 30 and 300) was reported although all counts were recorded in the lab book. The resulting data, which reflects averages of several runs, is shown in the plot of FIG. 7.

EXAMPLE 4

Example 4 goes farther, showing the removal of PPV at a wavelength of 308 nm. See summary FIG. 12, which includes data at 282 nm from tables 2 and 3. Removal rates are significantly faster than those at 282 nm. This surprising result can be explained by considering both the germicidal efficacy of the light. Considering standard action spectrum for UV disinfection and the closely related DNA absorption curve, 308 nm light is less efficient than 260 nm light by a factor of 10-20, and less efficient than light at 282 nm by a factor of approximately 5. This is more than counter acted by the substantial change in the absorption characteristics of platelets and plasma between 260 and 300 nm. The optical density decreases by a factor of 20—the data in table 3/FIG. 12a-12b show that this increase in transmission more than compensates for the decreased germicidal efficacy. FIG. 13 illustrates that the reduced absorption by platelets and plasma at 308 nm results in significantly less damage as well as increased viral inactivation. This surprising result is further supported by the appreciation of the importance of scattering discussed earlier in this disclosure.

Having thus described preferred embodiments and exemplary uses/applications of the present disclosure, it is to be understood that the specifically disclosed forms are merely illustrative of the scope of the present disclosure. Various changes may be made in the function and arrangement of parts and processing parameters; equivalent means may be substituted for those described and/or illustrated; and certain features may be used independently from others without departing from the spirit and scope of the invention as defined in the claims that follow.

The invention claimed is:

1. A method for sterilizing a complex fluid, comprising;
   a) introducing a supply of complex fluid into a treatment zone, wherein said complex fluid is selected from the group consisting of blood products, pharmaceuticals, injectable solutions and vaccines, said complex fluid containing a pathogen comprising a bacteria and/or a virus that is responsive to light energy;
   b) applying light energy to said complex fluid in said treatment zone, said light energy being supplied from an excimer, non-pulsed, non-laser light source utilizing dielectric barrier discharge that generates a substantially monochromatic light having a wavelength of between 260 nm and 310 nm;
   wherein said light energy from said light source is effective to substantially excite and inactivate said pathogen while substantially preserving said complex fluid; and wherein the light source is maintained at ambient temperature.

2. The method according to claim 1, further comprising adding a photoactive compound to said complex fluid prior to applying said monochromatic light thereto.

3. The method according to claim 1, wherein said light source includes a system for controlling temperature of said complex fluid throughout application of said monochromatic light thereto.

4. The method according to claim 1, wherein said light source generates said monochromatic light utilizing an excimer gas selected from the group consisting of XeI, $Cl_2$, XeBr, $Br_2$, XeBl, filtered XeBr, $I_2$ and XeF.

5. The method according to claim 1, wherein said complex fluid is a blood product and the method further comprises leukocyte reduction.

6. The method according to claim 1, wherein said complex fluid sterilization comprises the inactivation of said pathogen by disrupting one or more nucleic acids of said pathogens.

7. The method according to claim 1, wherein said complex fluid is a blood product selected from the group consisting of whole blood, plasma, platelets, packed cells and combinations thereof.

8. The method according to claim 2, wherein said complex fluid sterilization comprises excitation of the photoactive compound, wherein said excited photoactive compound is effective at inactivating said one or more pathogens; and said complex fluid is not affected by said excited photoactive compound.

9. The method according to claim 1, further comprising mixing said complex fluid during said sterilization thereof.

10. A method for inactivating a nucleic acid in a pathogen that contaminates a complex fluid comprising:
    a) introducing a supply of complex fluid into a treatment zone, wherein said complex fluid is selected from the group consisting of blood products, pharmaceuticals, injectable solutions and vaccines, said complex fluid containing a pathogen comprising a bacteria and/or a virus
    b) adding a photoactive compound to said complex fluid; and
    c) applying light energy to said complex fluid and said photoactive compound in said treatment zone, said light energy being supplied from an excimer non-pulsed, non-laser light source utilizing dielectric barrier discharge that generates a substantially monochromatic light having a wavelength less than 340 nm; wherein said light energy from said light source is effective to substantially excite said photoactive compound thereby disrupting said nucleic acid and inactivating said pathogen, while substantially preserving said complex fluid; and wherein the light source is maintained at ambient temperature.

11. The method according to claim 10, wherein said photoactive compound is riboflavin.

12. The method according to claim 10, wherein said nucleic acid excited by said light energy from said light source is single stranded.

13. The method according to claim 10, wherein said photoactive compound is effective at inactivating pathogens with double stranded nucleic acid.

* * * * *